United States Patent [19]

George, Jr. et al.

[11] Patent Number: 5,728,526
[45] Date of Patent: Mar. 17, 1998

[54] METHOD FOR ANALYZING A NUCLEOTIDE SEQUENCE

[75] Inventors: Albert L. George, Jr.; Satish K. Bhatnagar; Irina Nazarenko, all of Gaithersburg, Md.

[73] Assignee: Oncor, Inc., Gaithersburg, Md.

[21] Appl. No.: 472,239

[22] Filed: Jun. 7, 1995

[51] Int. Cl.⁶ .............................. C12Q 1/68; C12P 19/34; C07H 21/04
[52] U.S. Cl. .............................. 435/6; 435/911; 435/912; 536/243; 536/24.31; 536/24.32; 536/24.33
[58] Field of Search .............................. 435/6, 91.2, 91.1, 435/24.3, 24.31; 536/24.32, 24.33

[56] References Cited

U.S. PATENT DOCUMENTS

| | | | |
|---|---|---|---|
| 4,656,127 | 4/1987 | Mundy | 435/6 |
| 4,683,202 | 7/1987 | Mullis | 435/91 |
| 4,988,617 | 1/1991 | Landegren et al. | |
| 5,427,930 | 6/1995 | Birkenmeyer et al. | 435/91.52 |

FOREIGN PATENT DOCUMENTS

| | | |
|---|---|---|
| 185494 | 6/1986 | European Pat. Off. |
| 246864 | 11/1987 | European Pat. Off. |
| 439182 | 7/1991 | European Pat. Off. |
| WO90/01069 | 2/1990 | WIPO |
| WO 93/00447 | 1/1993 | WIPO |
| WO93/02216 | 4/1993 | WIPO |
| WO95/21271 | 8/1995 | WIPO |

OTHER PUBLICATIONS

Debuire et al, "Fast, Manual, Nonradioactive method for DNA sequencing", Clin. Chem. 39(8):1682–1685, 1993.
Fiore et al, (1988), "The Abbott IMx automated benchtop immunochemistry analyzer system", Clin. Chem. 34(9):1726–2732.
Matthews et al, (1988), "Analytical strategies for the use of DNA probes", Anal. Biochem. 169:1–25.
Southern et al, (1992), "Analyzing and comparing nucleic acid sequences by hybridization to arrays of oligonucleotides: Evaluation using experimental models", Genomics 13:1008–1017.
Stratagene Catalog, (1993) p. 105.
Weisberg et al, (1993), "Simultaneous mutagenesis of multiple sites: Application of ligation chain reaction using PCR products instead of oligonucleotides", Biotechniques 15(1):68–74.
Cotton et al, (1993), "Current Methods of mutation detection", Mutation Res. 285:135–144.
Abravaya et al, (1995), "Detection of point mutations with a modified ligase chain reaction (Gap–LCR)", Nucleic Acids Res. 23(4):675–682.
D.J. Picketts et al, *Human Genetics*, "Differential Termination of Printer Extension: A Novel, Quantifiable Method for Detection of Point Mutations", vol. 89, pp. 155–157 (1992).
E. Winn–Deen et al, *Poster Presentation–ASHG Annual Meeting*, "High Density Multiplex Mutation Analysis Using the Oligonucleotide Ligation Assay (OLA) and Sequence–Coded Separation", Abstract #1512, pp. 1–4 (1993).

M. Goldrick Ph.D., *Ambion TechNotes*, "Faster Mutation Analysis", vol. 2, No. 1, pp. 1 and 10.
R. Youil et al, *Proc. Natl. Acad. Sci. USA*, "Screening for Mutations by Enzyme Mismatch Cleavage with T4 Endonuclease VII", vol. 92, pp. 87–91 (1995).
A–Lien Lu et al, *Genomics 14*, "Detection of Singe DNA Base Mutations with Mismatch Repair Enzymes", pp. 249–255 (1992).
E.M. Southern et al, *Genomics 13*, "Analyzing and Comparing Nucleic Acid Sequences by Hybridization to Arrays of Oligonucleotides: Evaluation Using Experimental Models", pp. 1008–1017 (1992).
A. Pease et al, *Proc. Natl. Acad. Sci. USA*, "Light–Generated Oligonucleotide Arrays for Rapid DNA Sequence Analysis", vol. 91, pp. 5022–5026 (1994).
J. Dianzani et al, *TIG*, "Dilemmas and Progress in Mutation Detection", vol. 9, No. 12, pp. 1–3, (1993).
S. Borman, *C&EN, Science/Technology*, "'DNA Chips' Under Development for Sequencing Applications", pp. 24–25 (1994).
N. Dolinnaya et al, *Nucleic Acids Research*, "Oligonucleotide Circularization By Template–Directed Chemical Ligation", vol. 21, No. 23, pp. 5403–5407 (1993).
N. Dolinnaya et al, *Nucleic Acids Research*, "Structural and Kinetic Aspects of Chemical Reactions in DNA Duplexes. Information on DNA Local Structure Obtained From Chemical Ligation Data", vol. 19, No. 11, pp. 3073–3080 (1991).
N. Dolinnaya et al, *FEBS 09843*, "Probing DNA Triple Helix Structure by Chemical Ligation", vol. 284, No. 2, pp. 232–34 (1991).
N. Dolinnaya et al, *Nucleic Acids Research*, "The Use of BrCN for Assembling Modified DNA Duplexes and DNA–RNA Hybrids; Comparison with Water–Soluble Carbodiimide", vol. 19, No. 11, pp. 3067–3072 (1991).
S. Nilsson et al, *Nucleic Acids Research*, "Sealing of Gaps in Duplex DNA T4 DNA Ligase", vol. 10, No. 5, (7 pages included, no page numbers) (1982).

*Primary Examiner*—W. Gary Jones
*Assistant Examiner*—Jeffrey Fredman
*Attorney, Agent, or Firm*—Glenn E. Karta

[57] ABSTRACT

A method for analyzing a target nucleotide sequence which exists in a first state or a different second state which makes the method particularly useful for determining point mutations. The method uses a first polynucleotide which is immobilized on a solid support and which is at least partially complementary to a first segment of the target nucleotide sequence. By means of a series of steps, a product of the first polynucleotide and a further polynucleotide that contains a detectable label can be obtained. When the state to be analyzed occurs in a rare population, amplification can be conducted so that substantially only amplification of the target nucleotide sequence in one of the states is attained. The method can be used to analyze multiple target sequences simultaneously. A kit which can be used in the method is also set forth.

38 Claims, 13 Drawing Sheets

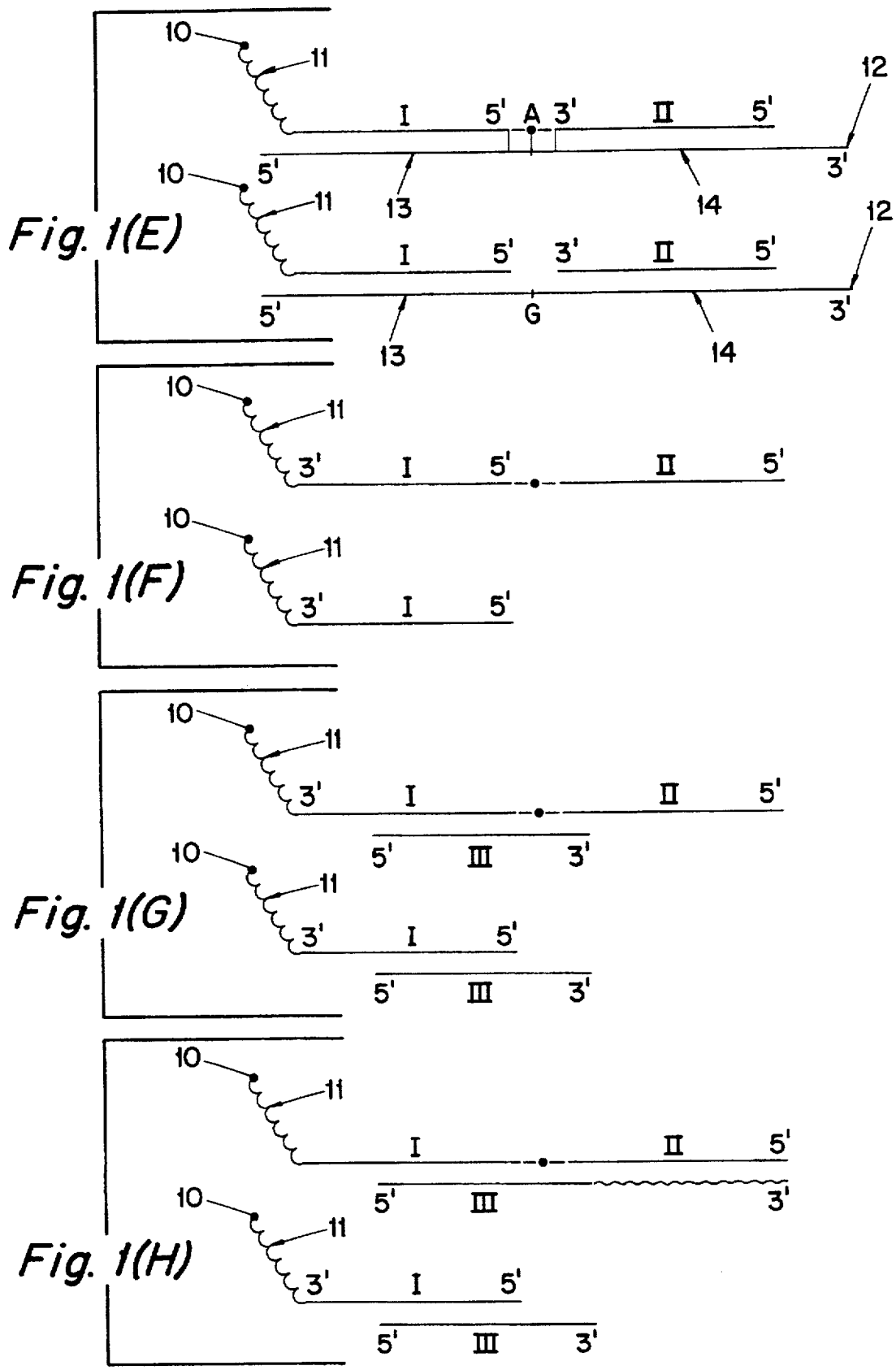

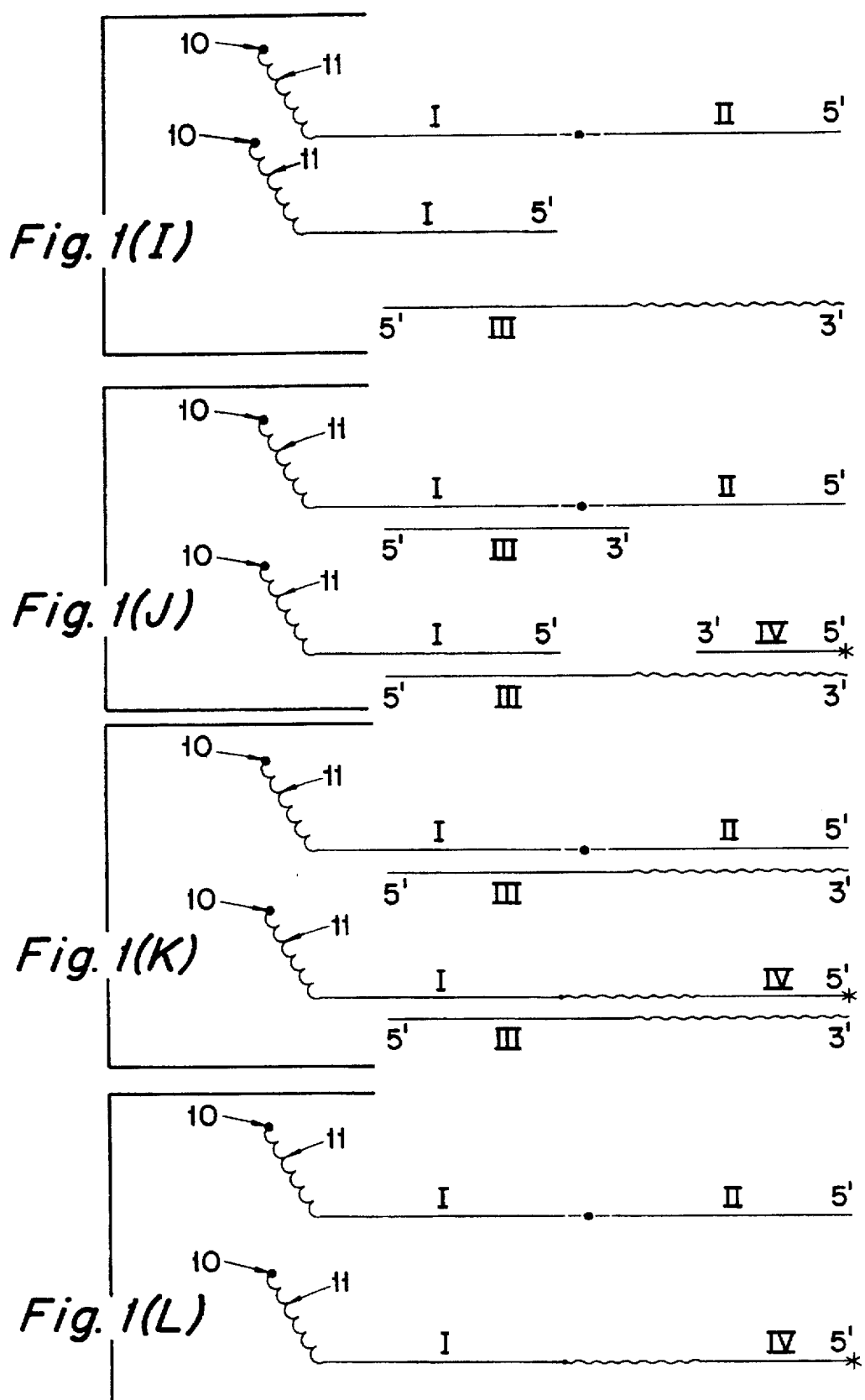

Fig. 2(A)
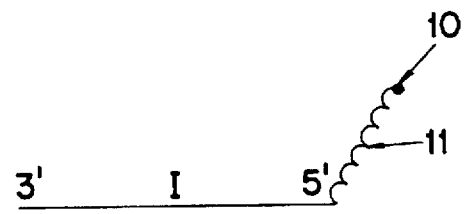
Fig. 2(B)
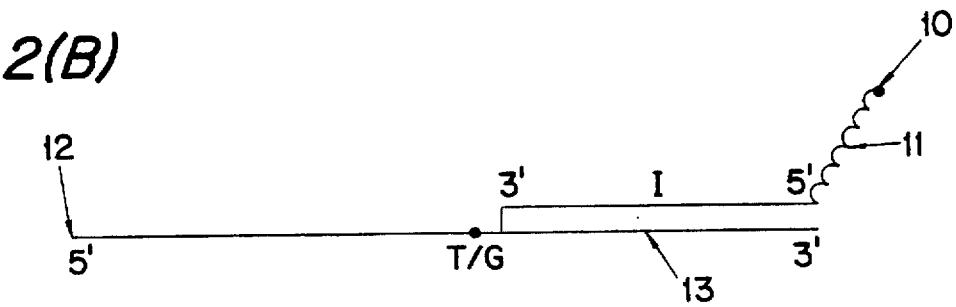
Fig. 2(C)
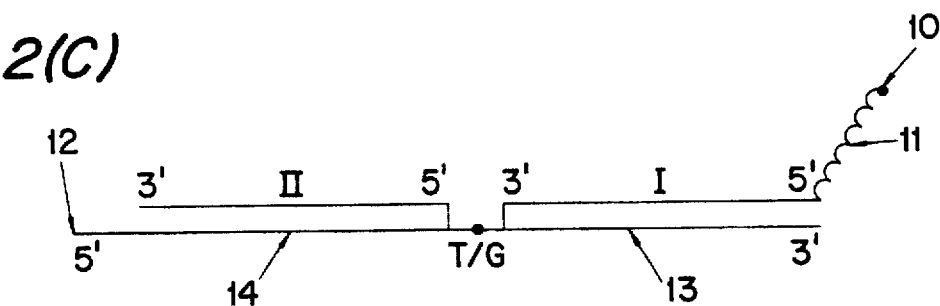
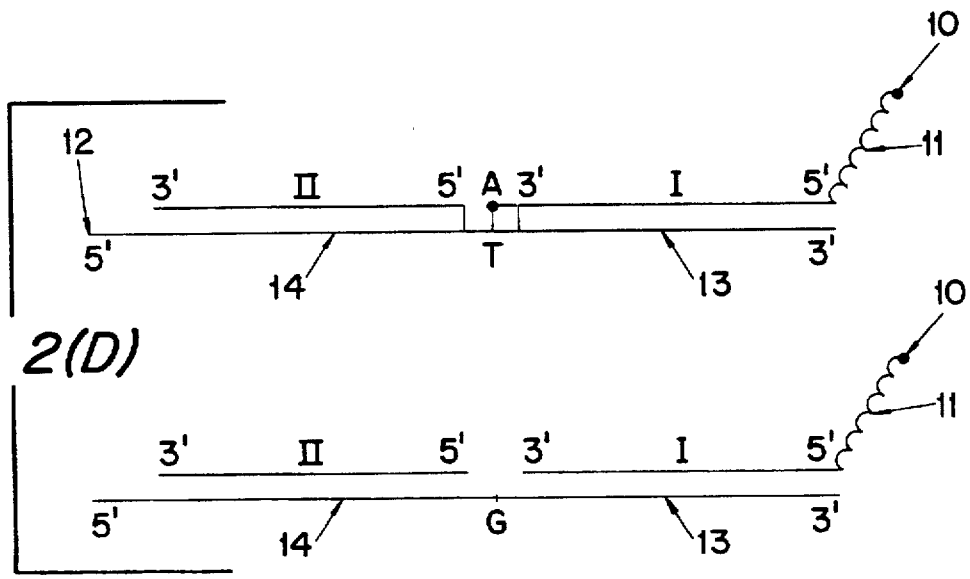
Fig. 2(D)

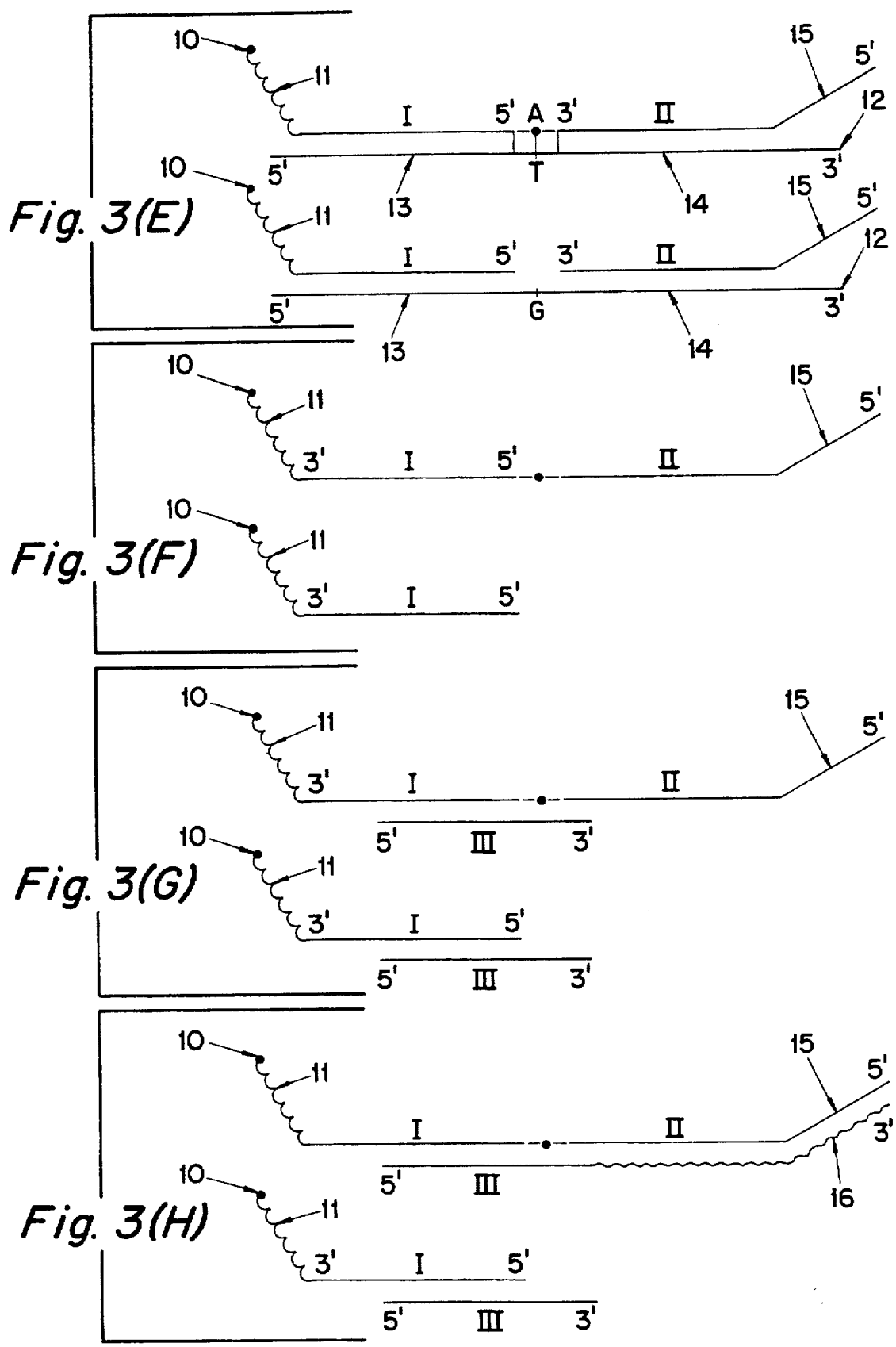

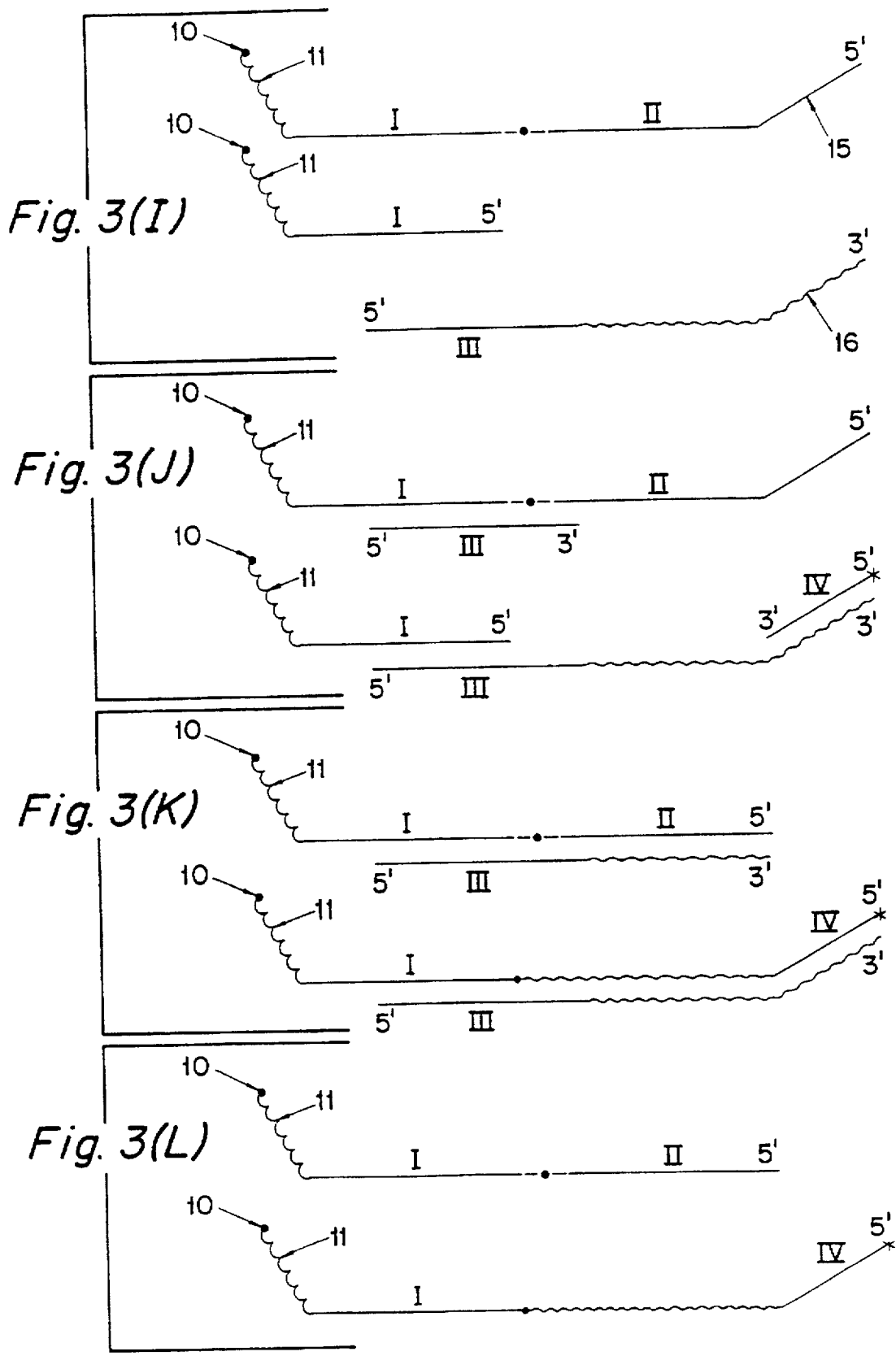

Fig. 4(A)

```
TGTTGGGGGA GGGGCCTCCT CCTCTGCAGG CCCAGGTGAC CCAGGGTTGG AAGCGTCTCA   60
TGCTGGATCC CCACTTTTCC TCTTGCAGCA GCCAGACTGC CTTCCGGGTC ACTGCCATGG  120
AGGAGCCCGCA GTCAGATCCT AGCGTCGAGC CCCCTCTGAG TCAGGAAACA TTTTCAGACC  180
TATGGAAACT GTGAGTGGAT CCATTGGAAG GGCAGGCCAC CACCCCGACC CCAACCCCAG  240
CCCCCTAGCA GAGACCTGTG GGAAGCGAAA ATTCATGGGA CTGACTTTCT GCTCTGTCT   300
TTCAGACTTC CTGAAAACAA CGTTCTGGTA AGGACAAGGG TTGGGCTGGG ACCTGGAGGG  360
CTGGGGGGGC TGGGGGGCTG AGGACCTGGT CCTCTGACTG CTCTTTTCAC CCATCTACAG  420
TCCCCCCTTGC CGTCCCAAGC AATGGATGAT TTGATGCTGT CCCCGGACGA TATTGAACAA  480
TGGTTCACTG AAGACCCAGG TCCAGATGAA GCTCCCAGAA TGCCAGAGGC TGCTCCCCGC  540
GTGGCCCCTG CACCAGCAGC TCCTACACCG GCGGCCCCTG CACCAGCCCC CTCCTGGCCC  600
CTGTCATCTT CTGTCCCTTC CCAGAAAACC TACCAGGGCA GCTACGGTTT CCGTCTGGGC  660
TTCTTGCATT CTGGGACAGC CAAGTCTGTG ACTTGCACGG TCAGTTGCCC TGAGGGGCTG  720
GCTTCCATGA GACTTCAATG CCTGGCCGTA TCCCCCCTGCA TTTCTTTTGT TTGGAACTTT  780
GGGATTCCTC TTCACCCTTA                                              800
```

Fig. 4(B)

```
AGGAGGTGCT TACACATGTT TGTTTCTTTG CTGCCGTGTT CCAGTTGCTT TATCTGTTCA   60
CTTGTGCCCT GACTTTCAAC TCTGTCTCCT TCCTCTTCCT ACAGTACTCC CCTGCCCTCA  120
ACAAGATGTT TGCCAACTG GCCAAGACCT GCCCTGTGCA GCTGTGGGTT GATTCCACAC  180
CCCCGCCCGG CACCCGCGTC CGCGCCATGG CCATCTACAA GCAGTCACAG CACATGACGG  240
AGGTTGTGAG GCGCTGCCCC CACCATGAGC GCTGCTCAGA TAGCGATGGT GAGCAGCTGG  300
GGCTGGAGAG ACGACAGGGC TGGTTGCCCA GGGTCCCCAG GCCTCTGATT CCTCACTGAT  360
TGCTCTTAGG TCTGCCCCCT CCTCAGCATC TTATCCGAGT GGAAGGAAAT TTGCGTGTGG  420
AGTATTTGGA TGACAGAAAC ACTTTTCGAC ATAGTGTGGT GGTGCCCTAT GAGCCGGCTG  480
AGGTCTGGTT TGCAACTGGG GTCTCTGGGA GGAGGGGTTA AGGGTGGTTG TCAGTGGCCC  540
TCCGGGTGAG CAGTAGGGGG GCTTTCTCCT GCTGCTTATT TGACCTCCCT ATAACCCCAT  600
```

METHOD FOR ANALYZING A NUCLEOTIDE SEQUENCE

BACKGROUND OF THE INVENTION

1. Field of the Invention

The present invention relates to an improved method for analyzing a nucleotide sequence which uses a polynucleotide fixed on a solid support and is capable of forming a product containing a detectable label. The present invention also relates to a kit for conducting the aforementioned method.

2. Description of the Related Art

In order to detect the existence or absence of a known nucleotide sequence, the art has developed different types of nucleic acids probes that contain a radioisotopic or non-radioisotopic label. The nucleic acid probes can be used to detect a particular gene in a cell, the alteration of which can be indicative of a particular symptom, to determine the presence of mRNA transcripts, or to determine the existence or absence of organisms such as viruses and bacteria. Radioisotope-labeled probes were originally extensively utilized, but are now being replaced with non-isotopic probes due to the potential health and environmental problems associated with the handling, storage, use and disposal of the former type of probes. However, the non-radioisotopic probes generally do not have the same degree of sensitivity as the radioisotopic probes.

One goal of analyzing nucleotide sequences is to determine if there is a mutation in the genetic code which will cause an inheritable disease. Detection of mutations is often complex and the art has developed a variety of different techniques in an attempt to provide a safe, reliable, and efficient way of determining whether a mutation is present. A summary of different techniques is set forth by I. Dianzani et al in Trends In Genetics, December 1993, Vol. 9, No. 12, pages 403–405. The described techniques include:

1) The use of allele-specific oligonucleotides wherein two perfectly complementary oligonucleotides bind more strongly to the target sequence than do two oligonucleotides with a single base-pair mismatch so that differential washing permits mutations to be detected;
2) The use of allele specific amplification wherein polymerase chain reaction primers that are complementary to the sequence where the mutation is located can be used to assay for the mutant or the wild-type allele based on the understanding that amplification will only occur if there is no mismatch between the primer and the target;
3) The use of a polymerase chain reaction primer that extends up to the base that is located 5' to the base that can exist in the mutated allele which can then be extended only if the complementary nucleotide is provided in the reaction mixture; and
4) The use of two oligonucleotides abutting each other that can be joined by ligase, which can be assayed, or that will be prevented from being joined by the occurrence of a mismatch at the 3' end of the 5' primer.

A further technique for detecting mutations is set forth in U.S. Pat. No. 4,656,127. In this technique, a labelled probe is hybridized to the target sequence so that one end of the probe is positioned adjacent the specific base where the mutation can exist. A nucleotide derivative, such as a thionucleotide, is added under conditions to cause it to join to the end of the probe if it is complementary to the specific base. The resulting hybrid is subjected to digestion using an exonuclease enzyme under conditions such that the nucleotide derivative protects the probe from digestion so that the subsequent observance of the label is indicative of the specific base.

In another technique, competitive oligonucleotide ligation is conducted with i) a dye-labeled common probe that is complementary to the sequence adjacent the base where mutation can exist, ii) a normal probe that is complementary with the normal sequence, and iii) a mutant probe that is complementary with the mutant sequence. The normal probe and mutant probe also contain tails (e.g., of hexaethylene oxide) of different length so that they have different electrophoretic mobility. In this way, multiplex mutation analysis can be conducted by both color and electrophoretic mobility.

In published European Patent Application No. 246,864, a method for discriminating a specific base sequence from a variant base sequence is described. The method involves subjecting adjacent segments of a target base sequence to hybridization with a detectable first nucleotide probe and with second nucleotide probe to form a hybrid. The nucleotide sequence of the first and second nucleotide probes are selected such that where they form a split probe hybrid with a complementary target sequence, they can be subsequently linked. The hybrid is subjected to linkage and detection.

In U.S. Pat. No. 4,988,617, a method of detecting a nucleotide change in nucleic acids is described. The method involves the use of oligonucleotide probes that are selected to anneal immediately adjacent segments of a substantially complementary test DNA or RNA molecule with the end of one probe being complementary to the normal or abnormal nucleotide. A linking agent is added under conditions such that when the target nucleotide is correctly base paired, the oligonucleotide probes are joined.

A different technique which detects mutations in double stranded DNA involves the use of a DNA mismatch-binding protein is set forth in published PCT application No. WO 93/02216. Upon binding the protein to the mismatch and amplification, the mismatch can be detected. The detection of certain single DNA base mutations can also be conducted using mismatch repair enzymes, particularly MutY protein, when the mutations occur in as little as 1% of the mutant sequence as described in A-Lien Lu et al Genomics 14, 249–255 (1992).

Current technology permits the detection of mutations by the above-mentioned techniques. These known techniques are limited, however, because they are unable to accurately detect mutations that occur in only a few cells in a background of normal cells.

OBJECTS AND SUMMARY OF THE INVENTION

It is therefore a general object of the present invention to provide an improved method for analyzing a nucleotide sequence.

It is a more specific object of the present invention to provide a method for analyzing a nucleotide sequence which uses a first polynucleotide which is immobilized on a solid support and which is complementary to a portion of a target nucleotide sequence.

It is another object of the present invention to provide a method for analyzing a nucleotide sequence that can have a single nucleotide mutation.

It is a further object of the present invention to provide a method of simultaneously analyzing multiple base positions, even in multiple genes.

It is a still further object of the present invention to provide a method for analyzing a nucleotide sequence which can accurately determine the sequence from a rare population of cells.

It is a yet further object of the present invention to provide a method for the early detection of cancers, genetic diseases and infectious diseases.

It is another object of the invention to provide a kit for analyzing a nucleotide sequence.

Accordingly, in one aspect, the present invention provides a method for analyzing a target nucleotide sequence having a first segment, a second segment and a third segment therebetween which is formed of at least one nucleotide but which is formed of less than four different nucleotides wherein the third segment has a nucleotide or nucleotide sequence in a first state or a different second state. The method comprises:

a) providing a first polynucleotide which is immobilized on a solid support and which is at least partially complementary to the first segment of the target nucleotide sequence;

b) hybridizing the first polynucleotide to the first segment of the target nucleotide sequence under conditions suitable for hybridization;

c) providing a second polynucleotide which is at least partially complementary to the second segment of the target nucleotide sequence;

d) hybridizing the second polynucleotide to the second segment of the target nucleotide sequence under conditions suitable for hybridization wherein a gap of at least one nucleotide is present between one end of the first polynucleotide and one end of the second polynucleotide;

e) providing at least one nucleotide selected such that all the nucleotides which are complementary to the third segment are provided for only one of the first state or the second state and less than all the nucleotides complementary to the third segment are provided for the other state, the nucleotide or nucleotides being provided under conditions whereby the nucleotide or nucleotides form an extended portion of one of the first or second polynucleotides that is complementary to the nucleotides(s) of the third segment of the target nucleic acid sequence in one of the states;

f) linking the polynucleotide with the extended portion to the other polynucleotide under conditions whereby a fused product is formed comprised of the first polynucleotide, the second polynucleotide and the extended portion therebetween;

g) separating the fused product from the target nucleotide sequence and non-linked second polynucleotide;

h) amplifying at least a portion of the fused product wherein the portion contains the extended portion under conditions suitable to form an amplified product containing the first polynucleotide and a detectable label, the amplifying being conducted to obtain a sufficient quantity of amplified product to detect the detectable label; and i) detecting the presence of the label of the amplified product.

In another aspect, the present invention provides a method for analyzing a target nucleotide sequence having a first segment, a second segment and a third segment therebetween which is formed of at least one nucleotide but which is formed of less than four different nucleotides wherein the third segment has a nucleotide or nucleotide sequence in a first state or a different second state. The method comprises:

a) providing a first polynucleotide which is immobilized on a solid support and which is at least partially complementary to the first segment of the target nucleotide sequence;

b) providing a second polynucleotide which is at least partially complementary to the second segment of the target nucleotide sequence;

c) hybridizing at least one of the first polynucleotide to the first segment and the second polynucleotide to the second segment of the target nucleotide sequence under conditions suitable for hybridization;

d) providing at least one nucleotide selected such that all the nucleotides which are complementary to the third segment are provided for only one of the first state or the second state and less than all the nucleotides complementary to the third segment are provided for the other state, the nucleotide or nucleotides being provided under conditions whereby the nucleotide or nucleotides form an extended portion of one of the first or and second polynucleotide that is complementary to the nucleotides(s) of the third segment of the target nucleic acid sequence in one of the states and wherein at least one of a provided nucleotide and the second polynucleotide contain a detectable label;

e) linking the extended portion to the other of the first or second polynucleotide so as to form a labeled fused product; and f) detecting the presence of the label of the fused product.

Other aspects relating to the method of the invention are set forth in the specification and claims.

In a further aspect, the present invention provides a kit for analyzing a target nucleotide sequence having a first segment, a second segment and a third segment therebetween which is formed of at least one nucleotide but which is formed of less than four different nucleotides wherein the third segment has a nucleotide or nucleotide sequence in a first state or a different second state. The kit comprises:

a) a first polynucleotide which is immobilized on a solid support and which is at least partially complementary to the first segment of the target nucleotide sequence, b) a second polynucleotide which is at least partially complementary to the second segment of the target nucleotide sequence;

c) at least one nucleotide selected such that all the nucleotides which are complementary to the third segment are provided for only one of the first state or the second state and less than all the nucleotides complementary to the third segment are provided for the other state;

d) reagents suitable for forming a fused product from the first polynucleotide, second polynucleotide and the nucleotide(s);

e) a third polynucleotide complementary to at least a portion of the first polynucleotide or at least a portion of the second polynucleotide and which is capable of being extended so that it has a portion which is complementary to the other of the first or second polynucleotide;

f) material suitable for forming a product of the first polynucleotide which is complementary to at least a portion of the extended third polynucleotide, said product containing a detectable label; and g) reagents suitable for hybridizing the third polynucleotide to at least a portion of the first polynucleotide or second polynucleotide, for extending the third polynucleotide, and for forming the labeled product of the first polynucleotide.

BRIEF DESCRIPTION OF THE DRAWINGS

FIGS. 1(A)-(L) illustrate a sequence of steps in accordance with one aspect of the present invention.

FIGS. 2(A)-(L) illustrate a sequence of steps in accordance with a further aspect of the present invention.

FIGS. 3(A)-(L) illustrate a sequence of steps in accordance with a still further aspect of the present invention.

FIGS. 4A and 4B [SEQ. ID NOS.: 1–2] illustrate portions of the genomic DNA sequence of the human p53 gene and possible points of mutation.

DESCRIPTION OF THE PREFERRED EMBODIMENTS

Figure 1A:
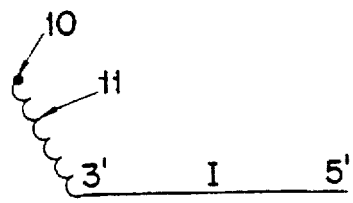

As noted above, one aspect of the present invention relates to a method for analyzing a target nucleotide sequence. The target nucleotide sequence can be RNA or DNA which has been previously analyzed so that the sequence of nucleotides being investigated is known. The method can be used to analyze the entire sequence of a known gene or a portion of a known gene. The method can also be used to analyze infectious diseases or to determine if a sample is from a particular source, such as for criminal investigations or parental determination. However, it is more preferred to use the method to determine the existence or absence of mutations consisting of one or a few nucleotides. Such mutations are known to code for such genetic diseases as sickle-cell anemia, hemophilia B, ADA deficiency, adrenal hyperplasia, diabetes, leprechaunism, phenyketonuria, and Tay-Sachs disease. In addition, mutations in genes can indicate the presence of cancer or a predisposition to develop cancer. For instance, over 60% of solid tumors in humans have mutations in the p53 gene. An extensive list of diseases, the gene and base change causing the disease and literature references describing them is set forth in Table 1 of Published PCT Application No. WO 93/02216, the contents of which are incorporated by reference.

The length of the target nucleotide sequence is generally selected to obtain the desired level of specificity. While the length of the target nucleotide sequence is not critical, it generally ranges from about 100 to about 200 bases, preferably from about 50 to about 100 bases and most preferably from about 31 to about 60 bases. The target nucleotide sequence has a first segment, a second segment and a third segment between the first segment and the second segment. The first and second segments are selected to have sufficient length so that polynucleotides which are at least partially complementary thereto have the desired degree of specificity. In general, the first and second segments are from about 50 to about 100 bases, preferably from about 25 to about 50 bases, most preferably from about 15 to about 25 bases in length. The first and second segments may or may not have the same number of bases.

The third segment is located between the first segment and the second segment. The third segment is at least one base in length and can be longer as long as it does not consist of all of the possible bases of the target sequence. Thus, for instance, when the target sequence is DNA, the third segment cannot consist of all of deoxythymidine monophosphate (dTMP); deoxyadenosine monophosphate (dAMP); deoxyguanosine monophosphate (dGMP); and deoxycytidine monophosphate (dCMP). In those instances where the target nucleotide sequence contains a mutation, the mutation is located in the third segment of the target nucleotide sequence so that in one state, the third segment has the normal sequence which would code for the wild type allele and in the other state, the mutant sequence would exist which would code for the mutant allele. Thus, for instance, in analyzing whether a sequence which causes sickle-cell anemia by a single mismatch in the DNA sequence, the target nucleotide sequence is selected so that the point mutation is present in the third segment.

In the event that the target nucleotide sequence is provided in double stranded form, it is denatured so that the target nucleotide sequence is present as a single strand. In addition, the target nucleotide sequence can be, if desired, amplified in accordance with conventional techniques, such as polymerase chain reaction, as described in U.S. Pat. No. 4,683,202, or ligase chain reaction, as described in Published PCT Application No. WO 90/01069, the contents of which are hereby incorporated by reference. Amplification can also be conducted in accordance with a technique developed by Oncor, Inc. of Gaithersburg, Md. known as Triamplification that is described in U.S. patent application Ser. No. 08/010,433, filed on Jan. 27, 1993, the contents of which are also incorporated by reference.

An important feature of the present invention is the use of a first polynucleotide which is immobilized on a solid support and which is at least partially complementary to the first segment of the target nucleotide sequence. The solid support can be any material which can immobilize the first polynucleotide thereto while permitting hybridization to the first segment of the target nucleotide sequence and which resists detachment after hybridization upon washing. The solid support can be selected from the group consisting of glass, cellulosic material and polymeric material. The cellulosic material can be natural or modified celluloses, such as nitrocellulose or phosphocellulose, while the polymeric material can be polystyrene, polypropylene, polyethylene, dextran, polyamide, polyacrylamide and agarose. The preferred solid support material is a polymeric material, especially a polyolefin and particularly polypropylene. The solid support can be fashioned into various configurations which include microparticles, beads, porous and impermeable strips and membranes, microtiter plates and the like.

The first polynucleotide can be immobilized on the solid support by any technique, such as by covalent or non-covalent bonding that is achieved either directly or indirectly through a linker group, as long as the first polynucleotide remains available for hybridization to the first segment of the target nucleotide sequence. The linker group can be an alkyl chain, which may or may not contain unsaturation, an alkyl ether chain or a chain containing various groups, as long as the linker group does not adversely affect the ability of the first polynucleotide to hybridize with the first segment or otherwise affect the results of the analytic method. Subject to these provisos, it should also be apparent that the linker group can include one or more nucleotides that are not complementary to the first segment. This variation of the method can be used to simplify the reactants where multiple sequences are being analyzed. More specifically, if the portion of each of the first polynucleotides that is non-complementary to the respective first segments of the target sequence is the same sequence of nucleotides, then only a single type of third polynucleotide (discussed in greater detail below) that is complementary to the non-complementary portion of each of the first polynucleotides will be needed for each of the target sequences being analyzed.

A description of suitable solid supports and techniques which can be used to immobilize the first polynucleotide thereto are set forth in Published PCT Application No. WO 93/02216, the contents of which have been previously incorporated by reference. As described therein, one technique for immobilizing the first polynucleotide to a nitrocellulose support involves saturating a solution of the first polynucleotide with sodium iodide and spotting or filtering aliquots onto the nitrocellulose support. Alternatively, the first polynucleotide can be treated with glyoxal at a concentration of less than one molar, absorbed on the support and then fixed by baking at around 80° C. under vacuum for about 2-3 hours.

The aforementioned PCT application also describes covalent immobilization which includes coupling to phosphocellulose through phosphate groups activated by carbodiimide or carbonyldiimidazole or reactions of diazo groups on m-diazobenzoyloxymethyl cellulose with G and T residues of the first polynucleotide. The first polynucleotide can be mobilized on polysaccharide supports through phosphodiester links formed between a terminal phosphate of the polynucleotide and hydroxyl moieties of the support by water soluble carbodiimide activation or by coupling nucleophilic sites on the first polynucleotide with a cyanogen bromide-activated support. Additionally, for at least the terminal sugar group, the 3'-hydroxyl terminus of the first polynucleotide can be oxidized by periodate and coupled by Schiff base formation with supports bearing amine or hydrazide groups. Finally, supports having nucleophilic sites can be reacted with cyanuric chloride and then with the first polynucleotide.

An alternative technique of immobilizing the first polynucleotide to a glass support is described by E. M. Southern et al. *Genomics* 13, 1008–1017 (1992), the contents of which are incorporated by reference. In this technique, the first polynucleotide can be covalently attached to the surface of a glass plate via the use of a linker which is a primary aliphatic hydroxyl group attached to the glass through a chain comprising only stable carbon-carbon and aliphatic ether linkages. The polynucleotide is synthesized from the primary hydroxyl group using standard phosphoramidate or H-phosphonate chemistry.

The formation of reactive hydroxyl groups in selective areas using photolithographic techniques is described in A. C. Pease et al, Prc. Natl. Acad. Sci. U.S.A., Vol. 91, pp 5022–5026 (1995) and in C&EN, pp 24–25, Jun. 6, 1994, the contents of both of which are incorporated by reference.

A simple way of immobilizing the first polynucleotide to the solid support relies on the high affinity of biotin to streptavidin. In this technique, a base of the first polynucleotide, preferably the base which is located furthest from the third segment (e.g., possible point of mutation) can be modified to include a biotin molecule through a linker arm as described in the literature, such as in U.S. Pat. Nos. 4,711,955, 5,013,831 and 5,241,060, the contents of which are incorporated by reference. The solid support, such as in the form of beads, can be coated with streptavidin by techniques known in the art. Streptavidin-coated beads are commercially available by CPG Inc. of New Jersey or Dynal Inc. of New York. The biotin is then reacted with the streptavidin to bind the first polynucleotide to the solid support. Although the biotin-streptavidin system has been used in various labeling systems, the attachment of the first polynucleotide to the solid support in this manner does not constitute a label in the context of the present invention.

To understand further the various aspects of the present invention, reference is made to FIGS. 1(A)–(L) wherein common reference numbers indicate common materials. As may be seen from FIG. 1(A), the first polynucleotide indicated by I is immobilized on solid support 10 via a linker arm 11 which is selected so that the first polynucleotide is accessible for hybridization to the first segment of the target polynucleotide sequence. As noted above, the first polynucleotide can include a portion which is non-complementary to the first segment of the target sequence. In the illustrated embodiment of the invention, the first polynucleotide is immobilized to the solid support at the 3' end with its 5' end phosphorylated.

Figure 1B:
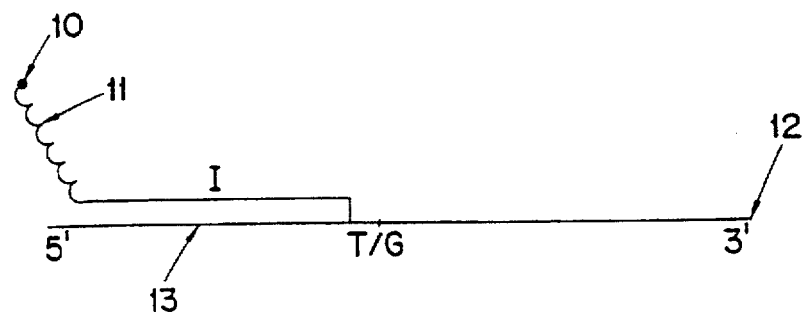

As illustrated in FIG. 1(B), a nucleotide sequence generally indicated by 12 which includes the target nucleotide sequence is provided and the first segment generally indicated at 13 is hybridized to the first polynucleotide. For purposes of illustration, the point mutation of the target nucleotide sequence has a first (mutant) state indicated by T and a second (normal) state indicated by G. As indicated above, the nucleotide sequence can be either RNA or DNA (including cDNA) and, if it is DNA, it is denatured so that a single strand containing the target nucleic acid sequence is provided.

While the target nucleotide sequence can be amplified by conventional techniques, such as polymerase chain reaction (PCR) or ligase chain reaction (LCR) prior to hybridization with the first polynucleotide immobilized on the solid support, it may be desirable to forego amplification, particularly by PCR, which can result in mutations in the amplified sequence. The amount of first polynucleotide immobilized on the solid support is preferably in substantial excess of the amount of target nucleotide sequence especially where amplification is subsequently conducted. While the relative amounts will vary depending on the particular situation, a general molar ratio of the first polynucleotide to the first segment of the target nucleotide sequence is at least 1:1, preferably at least about 1,000:1 and most preferably at least about 1,000,000:1.

Figure 1C:
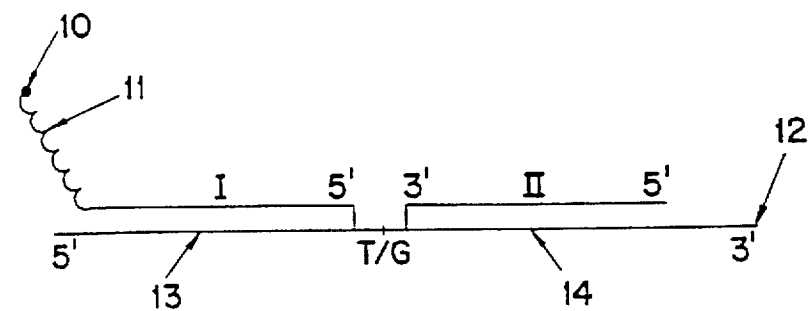

In FIG. 1(C), the second polynucleotide indicated by II is provided and hybridized to the second segment 14 of the target nucleotide sequence. In this illustrative embodiment, the hybridization of the second polynucleotide II to the second segment 14 of the target nucleotide sequence leaves a one nucleotide gap between the 3' end of the second polynucleotide and the 5' end of the first polynucleotide. The size of the gap and the relative sizes of the first and second polynucleotides are not drawn to scale. While the figures illustrate that the second polynucleotide is hybridized to the second segment after the first polynucleotide is hybridized to the first segment, the second polynucleotide can first be hybridized to the second segment, even before the target sequence is contacted with the immobilized first polynucleotide, or the first and second polynucleotides can be simultaneously contacted and hybridized with the first and second segments of the target sequence.

Figure 1D:
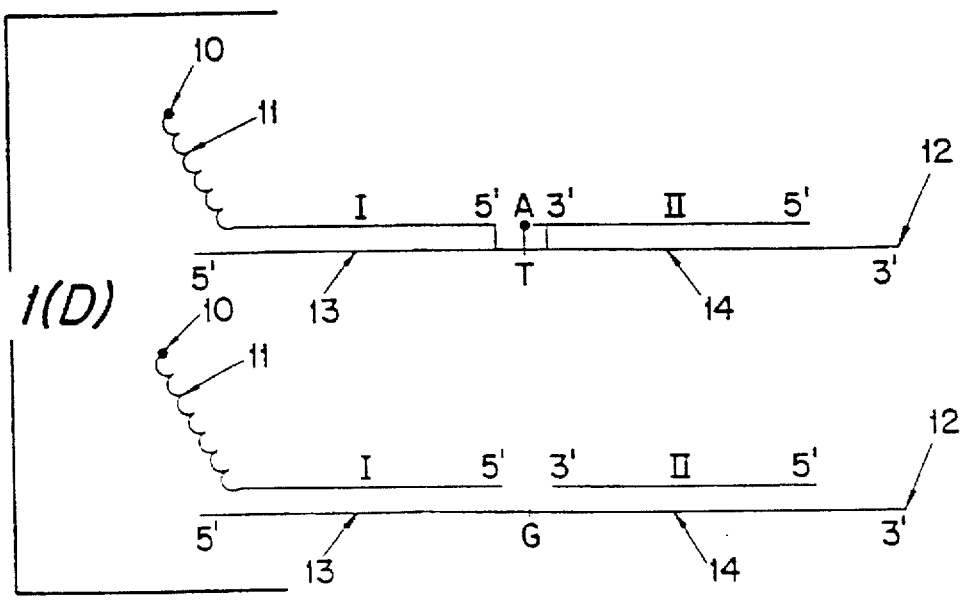

In FIG. 1(D), free nucleotide (i.e., dATP) is provided in the presence of polymerase under conditions such that the dATP will extend the 3' end of the second polynucleotide complementary to the T-nucleotide which forms the third segment in the mutant state of the target nucleotide sequence. The polymerase is preferably selected to provide the highest level of fidelity possible. Thus, for instance, for extending in the presence of dATP, the polymerase Pfu, commercially available from Stratagene, can be used. Where the third segment is in the normal state indicated by the G-nucleotide, no extension of the second polynucleotide will occur because a complementary nucleotide is not available. Consistent with the discussion set forth above, if the second polynucleotide is first hybridized with the second segment before the target sequence is hybridized with the immobilized first polynucleotide, the hybridized second polynucleotide can also be extended by the free nucleotide (s) before the target sequence is contacted with the mobilized first polynucleotide. If this variation is used, the immobilized first polynucleotide is selected so that one end is adjacent the last nucleotide added by the polymerase in one of the states so that it is capable of being ligated.

In FIG. 1(E), the extension of the second polynucleotide II is linked to the 5' end of the first polynucleotide I to form a fused product consisting of the first polynucleotide I, the second polynucleotide II and its extended portion A. Linking of the extended portion to the first polynucleotide is typically achieved using ligase or chemical ligation. When ligase is used, it is preferably selected to obtain the least level of background noise (i.e., linking of a portion that is non-complementary to the third segment). Additionally, techniques can be employed which reduce the possibility of ligation across a gap between the first and second polynucleotides. Since there is no nucleotide present to fill the gap when the third segment is in the normal state, the gap still remains where the first and second polynucleotides are bound to the target nucleotide sequence having a third segment in the normal state.

In the event that there is a sufficient quantity of the third segment in the mutated state to detect without amplification (e.g., approximately at least one in $10^2$ to $10^3$ occurrences), the method can use labeled nucleotide(s) that form at least part of the extended portion complementary to the third segment, labeled second polynucleotide or both (not shown). The detection of the mutated state is determined by the combined selectivity of the polymerase and the ligase. In this respect, since amplification cycles are not conducted, the polymerase and ligase can be chosen to obtain the highest level of fidelity without regard to the thermal stability of the enzymes. To even further reduce possible background signals caused by ligation across the gap, such as has been reported with T4 DNA ligase by Nilsson et al, Nucleic Acids Research, Vol. 10, No. 5, 1982, the 3' end of the polynucleotide adjacent the gap can be modified so that it is no longer a good substrate for ligase, but can still be extended by polymerase. Thus, only the extended polynucleotide will ligate to the 5' end of the other polynucleotide across the gap.

Modification of the 3' end of the polynucleotide adjacent the gap can be achieved by incorporating one or more ribo- or 2-O-methyl ribonucleotides as can be understood by those skilled in the art. As an alternative technique to avoid ligation across the gap, one can add a chain terminator which is complementary to the other (e.g., normal) state of the third segment. For instance, in the embodiment illustrated in FIG. 1(D), prior to the addition of the dATP, one would add dideoxycytidine triphosphate (ddCTP), as a chain terminator, and polymerase which would cause extension by dideoxycytidine monophosphate (ddCMP) which cannot be ligated. Excess ddCTP could then be removed by washing before the dATP is added. In this fashion, the ligation across a gap could again be inhibited. To facilitate incorporation of the chain terminator in the presence of DNA polymerase, the reaction can be conducted in the presence of manganese which can be used alone or in combination with other divalent cations. The concentration of the manganese in the reaction would typically be in the range of from 0.01 mM to 10 mM.

When both the nucleotide(s) and the second polynucleotide are labeled, the labels can be detected independently or can interact to provide a signal (e.g., by energy transfer) indicating the presence of both entities. The detection can be conducted with or without separating the target nucleotide sequence from the fused product.

In the event that the mutation cannot be detected without amplification (e.g., occurring on the order of one in $10^5$ to $10^6$ occurrences), the fused product illustrated in FIG. 1(E) is separated from the target nucleotide sequence and the non-linked second polynucleotide so as to provide the structures illustrated in FIG. 1(F) and at least a portion thereof is then amplified. Separating the fused product which is immobilized on the solid support 10 can be achieved by any treatment sufficient to separate the fused product from the target sequence such as by using exonuclease and denaturation. The denaturing conditions are selected to separate non-enzyme digested products from products fused to the first polynucleotide are well established in the art and can be achieved by selecting appropriate temperature or pH, using solvents, etc.

Separation may or may not include washing to remove materials not immobilized on the solid support. Washing can be avoided in certain circumstances (e.g., depending on the other polynucleotides used) by deactivating the terminal reactive site of the second polynucleotide. In the event that washing is used, it can be conducted by using deionized water and/or any other reagent that can be used to facilitate the removal of unbonded material. Such reagents can include organic solvents, buffers, detergents, salts, chaotropic agents, and other materials and/or techniques, such as the use of an electric field, known to those of ordinary skill in the art.

To amplify at least a portion of the fused product, any known technique can be used such as polymerase chain reaction, ligase chain reaction or a modification thereof such as by modifying the at least one probe/primer end as described in Published European Patent Application No. 439,182, the contents of which are incorporated by reference. Preferably, amplification is conducted in accordance with the aforementioned technique developed by Oncor, Inc. of Gaithersburg, Md. known as Triamplification which is distinct from known techniques and can enable amplification irrespective of whether the first polynucleotide is immobilized at or near its 3' or its 5' end.

The amplification is conducted to amplify at least a portion of the fused reaction product wherein the portion contains the extended portion. In this manner, amplification of the target state (e.g., the point mutation of the third segment) is attained. To provide one way of amplifying using Triamplification, FIG. 1(G) illustrates a third polynucleotide III which is provided and hybridized to the fused product immobilized on solid support 10 and the first polynucleotide on solid support 10. The amount of polynucleotide III is generally provided in molar excess of the amount of polynucleotide I, preferably at least a two-fold molar excess so as to improve the hybridization kinetics. As illustrated, the third polynucleotide III preferably is complementary to at least a portion of the first polynucleotide I and preferably is complementary to at least the extended portion of the second polynucleotide II. However, as noted above, especially where multiple target sequences are being simultaneously analyzed, each first polynucleotide can include an identical portion that is non-complementary to the first segment of the target sequence and the third polynucleotide can be complementary to this portion so that the same third polynucleotide can be used for each sequence being analyzed. This would simplify the method by reducing the number of different polynucleotides needed.

In FIG. 1(H), the third polynucleotide III is extended at its 3' end so that it is complementary to the remaining portion of the fused product immobilized on solid support 10. Extension of the third polynucleotide III (as indicated by the wavy line in the Figure) can be achieved by conventional techniques such as by adding DNA polymerase and all four deoxynucleosidetriphosphates when the target nucleotide sequence is DNA. With respect to the third polynucleotide III hybridized to the first polynucleotide, no extension of the third polynucleotide will occur, as also illustrated in FIG. 1(H), due to the absence of a template formed of the fused product.

Denaturing of the third polynucleotide III in its extended or nonextended form is then conducted so as to provided the structures illustrated in FIG. 1(I). Denaturing can be conducted under conventional conditions, such as by heating, which can separate the fused product from the extended third polynucleotide and the third polynucleotide from the first polynucleotide without adversely affecting the integrity of the polynucleotides.

In FIG. 1(J), additional third polynucleotide III, is hybridized to the fused product immobilized on solid support 10. In addition, the extended third polynucleotide III is hybridized to the first polynucleotide I mobilized on the solid support 10 and the fourth polynucleotide IV is hybridized to the extended portion of the third polynucleotide III. The fourth polynucleotide IV contains a detectable label indicated by an asterisk. While the label is indicated at the 5' end of the fourth polynucleotide IV, it can be located at any location and can exist as a plurality of labels as long as the labels do not affect the ability of the fourth polynucleotide IV to hybridize to the extended portion of the third polynucleotide III and to be extended and linked as discussed below. The amount of the fourth polynucleotide IV is not critical, but is generally selected such that it is at least equimolar to the amount of polynucleotide I and can be up to a ten-fold molar excess to improve the hybridization kinetics.

By extending the third polynucleotide III so that it is complementary to the fused product and by extending the fourth polynucleotide IV to the first polynucleotide I and linking, such as by using all four deoxynucleosidetriphosphates, DNA polymerase and DNA ligase when DNA is involved, amplification can be achieved so as to obtain an amplified product consisting of the labeled and extended fourth polynucleotide IV and the first polynucleotide I immobilized on the solid support 10. Additionally, further amounts of extended third polynucleotide III are obtained. The steps illustrated in FIGS. 1(G) through 1(K) can be repeated to obtain the desired amount of the amplified product. While the amount will vary depending on certain factors, such as the type of label, the amount of amplified product is sufficient to be detected. For instance, for fluorescent labeling, the typical current amount sought is typically at least about 100 molecules, preferably at least about 1,000 molecules.

While detection of the detectable label may be directly undertaken after the last round of amplification so that the amplified product is in duplex condition, it may be more desirable to denature and wash so that substantially only the products remaining on the solid support are the fused product and amplified product as illustrated in FIG. 1(L).

The presence of the detectable label of the amplified product will indicate the presence of the mutant state. However, it should be clear that by selecting the appropriate nucleotide, the normal state can be detected instead of the mutant state. It should also be apparent to those skilled in the art that while the present invention has been illustrated with respect to analyzing a single target nucleotide sequence, in some instances, multiple target sequences can be analyzed simultaneously by designing appropriate polynucleotides and detectable labels. One means of analyzing multiple target sequences at the same time is to use a grid wherein a plurality of different first polynucleotides are immobilized on each section of the grid. If point mutations are being analyzed, by providing only a single mononucleotide for each portion of the grid, the existence of multiple mutations can be analyzed simultaneously. This technique can be used to analyze the multiple sequences with or without amplification and can also be applied to third segments that are larger than a single mononucleotide by using appropriate combinations of mononucleotides as long as less than all the nucleotides are provided for one of the alternative states.

The present invention can potentially be used to analyze certain chromosomal aberrations. For instance, by using an appropriate first and/or second polynucleotide or by adding mononucleotides in a defined sequence, inversions may be subjected to analysis by the present invention. The analysis of inversions can also be conducted using appropriate grids of the type discussed above.

Aside from the apparent utility of determining mutations in nucleotide sequences to determine possible genetic defects, the present invention can provide an extremely valuable procedure to determine the extent and state of cancerous growth. By taking samples at various locations around a cancerous growth, the present invention can detect cancerous cells even though they exist in a very low concentration. The surgeon can then determine the extent of surgery necessary. Additionally, upon completion of surgery, samples can be taken from around the surgically removed area to ensure that there are no cancerous cells remaining. Compared to current techniques, the present invention can provide a higher level of accuracy by reducing background "noise" since essentially only the target sequence is detected or amplified and detected. The present invention can also be used to screen for cancerous cells or infectious diseases in blood, urine, sputum, stool and any other source. Moreover, the present invention can in many instances provide the results more rapidly and conveniently.

In the present invention, the polynucleotides can be prepared by any method known in the art. For instance, each of the polynucleotides can be prepared by chemical synthesis, or by cleavage of a larger nucleic acid using non-specific nucleic acid-cleaving chemicals or enzymes, or by using site-specific restriction endonucleases. The polynucleotides may also be prepared using the β-cyanoethylphosphoramidate method or other methods known in the art. A preferred method for synthesizing polynucleotides is conducted using an automated DNA synthesizer by methods known in the art. Once the desired polynucleotide is synthesized, it is cleaved from the solid support on which it was synthesized, and treated, by methods known in the art, to remove any protecting groups present. The polynucleotide may then be purified by any method known in the art, including extraction, gel purification and HPLC. The concentration and purity of the polynucleotide may be examined on an acrylamide gel, analytical HPLC or by measuring the optical densities at 260 and 280 nanometers in a spectrophotometer.

The nucleotides used in the present invention are selected depending on the particular situation. When the target nucleic acid sequence is DNA, the four different nucleotides which can be used in the invention are deoxythymidine triphosphate (dTTP); deoxyadenosine triphosphate (dATP); deoxyguanosine triphosphate (dGTP); and deoxycytidine triphosphate (dCTP). On the other hand, when the target nucleic acid sequence is RNA, the four different nucleotides are uridine triphosphate (UTP); adenosine triphosphate (ATP); guanosine triphosphate (GTP); and cytidine triphosphate (CTP). Alternatively, deoxyuridine triphosphate (dUTP), deoxyinosine triphosphate (dITP), inosine triphosphate (ITP) or any other modified base may replace one of the four nucleotides or may be included along with the four nucleotides as long as it does not adversely affect the desired objectives of the present invention. In addition to using the different nucleotides, reverse transcriptase is used when the target sequence is RNA.

Accordingly, the preparation of the extended polynucleotides illustrated in FIGS. 1(H) and 1(K) are generally conducted in the presence of the four deoxynucleotide triphosphates (dATP, dCTP, dGTP and dTTP) or a modified nucleoside triphosphate to produce the extended polynucleotide when the target nucleic acid sequence is a DNA strand, or in the presence of the four ribonucleoside triphosphates (ATP, CTP, GTP and UTP) or a modified nucleoside triphosphate to produce the extended polynucleotide when the target nucleic acid sequence is an RNA strand.

The extension of the polynucleotides with nucleotides is generally conducted in the presence of polymerase which may be any enzyme capable of polymerizing an RNA or DNA strand, including E. coli DNA polymerase I, the Klenow fragment of E. coli DNA polymerase I, T4 DNA polymerase, RNA polymerase or reverse transcriptase. In general, the polynucleotide is extended by the polymerase in a target dependent manner, for example, under conditions such that a nucleic acid strand is formed complementary to the nucleic acid sequence to which the polynucleotide is hybridized. Preferably, the polymerase is stable at temperatures of approximately 0°–95° C., such as Taq DNA polymerase (available from Perkin-Elmer Corporation, Norwalk, Conn.). Absent a thermally stable polymerase, the polymerase must be added again each time the cycle is repeated. However, as noted above, when amplification is not necessary, one can use a polymerase with higher fidelity without regard to its thermal stability. At least about 0.05 units of polymerizing enzyme (as defined by the manufacturer)/picomole of polynucleotide is generally used.

To provide even a higher level of fidelity and depending on the nucleotide(s) that will hybridize to the third segment, an endonuclease can be present in the reaction mixture that will correct any improper matches that may occur. For instance, if the third segment is G or C for the mutant state and is T for the wild state, and dATP is in the mixture, the MutY enzyme will remove the improper A/G or A/C mismatch which will lead to less background noise.

In some situations, it may be desired to modify the 5' end of the first polynucleotide to prevent the hydrolysis of the primer by a 5' to 3' exonuclease that can be associated with the polymerase. An exemplary modification can involve the placement of a phosphorothioate group between the last nucleotides of the 5' end of the polynucleotide. Methods for the chemical synthesis of phosphorothioate containing polynucleotides are known in the art (see e.g., Ott and Eckstein, Biochemistry, (1987) 26:8237–8241). Such a modification does not need to be removed prior to ligation of the first and second polynucleotides and the first and fourth polynucleotides.

The linking of the extended portions is generally conducted in the presence of ligase which may be any enzyme known in the art to ligate nucleic acid sequences, including viral ligases, such as T4 ligase, cellular ligases, such as E. coli ligase, but it is preferably a ligase stable at temperatures of approximately 0°–95° C., such as AMPLIGASE (available from Epicentre Technologies of Madison, Wis.) and Taq ligase (available from New England Biolabs of Beverly, Mass.). If amplification is conducted using a ligase and if a thermally stable ligase is not used, the ligase must be added again each time the cycle is repeated. Approximately at least 1 unit of ligating enzyme/picomole of polynucleotide is used. One unit is defined as the amount required to catalyze the ligation of 50% of the cos sites in one microgram of BstE II digested bacteriophage λ DNA in fifteen minutes at 45° C.

Alternatively, ligation can be conducted chemically by techniques known in the art. For instance, chemical ligation is described by N. Dolinnaya et al, Nucleic Acids Research, 1993, Vol. 21, No. 23, 5403–5407, N. Dolinnaya et al, Nucleic Acids Research, 1991, Vol. 19, No. 11, 3073–3080, N. Dolinnaya et al, Federation of European Biochemical Societies, 1991, Vol. 284, No. 2, 232–234, and N. Dolinnaya et al, Nucleic Acids Research, 1991, Vol. 19, No. 11, 3067–3072, the contents of which are incorporated by reference.

Hybridization is generally conducted at a temperature of approximately 10°–95° C., preferably 50°–75° C., more preferably 60°–70° C., and most preferably 63°–68° C. The period for each hybridization step depends on a number of variables, but can be approximately 0.5–20 minutes, preferably 1–15 minutes and most preferably approximately 1–5 minutes. The extension/ligation or the hybridization/extension/ligation steps are generally conducted at a temperature of approximately, 10°–95° C. preferably 60°–80° C. and more preferably 68°–78° C. for a period of 0.5–50 minutes, preferably 2–40 minutes, and most preferably 2–10 minutes.

The pH of the reaction medium is selected so that the various steps of the method can be conducted. For instance, the pH can be maintained by buffers so that it is preferably in the pH range of about 7.5–8.5, more preferably about 8–8.5, and most preferably about 8.0.

In order to conduct denaturation wherein complementary strands of nucleic acid are separated, any suitable denaturing method including well-known physical, chemical or enzymatic means can be used. For example, one physical method of separating the strands of the nucleic acid involves heating the nucleic acid until it is completely denatured. Typical heat denaturation is generally conducted at a temperature of approximately 85°–110° C., more preferably at 90°–100° C., and most preferably at about 92°–96° C. for a period of at least about 0.5 minutes. One skilled in the art would understand how to modify the temperatures and times so as to optimize the results obtained with different polynucleotides. Alternatively, denaturation can be achieved by other methods known in the art. One such method is by the introduction of a nucleic acid-unwinding enzyme such as helicase.

In those steps where one hybridized polynucleotide is extended and then linked to another hybridized polynucleotide, there is a possibility that the extension can displace the other hybridized polynucleotide before linking can occur. This so-called "strand displacement" phenomenon is related to the processivity of DNA polymerase which is defined as the number of nucleotide residues added per enzyme binding event. A DNA polymerase enzyme with a high degree of processivity will show a strong strand displacement activity. The processivity of the enzyme is affected by factors such as 1) salt concentration, 2) nucleotide concentration, and 3) divalent cations. It has been found that:

1) Increasing the salt concentration during polynucleotide extension will lower processivity thereby decreasing the tendency of strand displacement and promoting the tendency for linking (ligation) to occur.
2) Decreasing the nucleotide concentration of the residue of the 5'-end of the polynucleotide not being extended will cause the DNA polymerase to pause before incorporating the limiting nucleotide during extension which permits additional time for the DNA ligase to link the extension to the other polynucleotide.
3) Modifying the template to contain a modification at the proper position which causes polymerase to pause or dissociate at that position. In primer extension by DNA polymerase on a normal DNA template (containing one or more of deoxy adenosine, cytosine, guanosine, and thymidine monophosphate, and phosphodiester internucleotide linkages), the nucleotide incorporation is governed by Watson-Crick base pairing. Modification in the template could have an inhibitory effect on DNA polymerase activity. The possible mechanism for this arrest of DNA synthesis could be the distortion of the primer:template binding site or loss of base coding property at the modification site. Examples of some of the modifications in the template that can affect DNA polymerase are an abasic site, pyrimidine dimers, ribonucleotides, thymine glycol, arabinosylcytosine, etc., See Moore & Strauss, Nature, 278, 664–66 (1979); Sagher & Strauss, Biochemistry, 22, 4518–26 (1983); Clark & Beardsley, 1987; Mikita & Beardsley, Biochemistry, 27, 4698–4705 (1988), the contents of which are incorporated by reference.

Arrest of DNA chain elongation by incorporating a synthetic modification in the template can be applied to the present amplification technique for preventing strand displacement. A modification in DNA for the purpose of this technique can be defined as any modification in the DNA that will inhibit bypass by DNA polymerase. Examples of some of the modifications that can be easily incorporated into DNA are arabinosyl derivatives of AMP, CMP, GMP, TMP and UMP; ribonucleotides; 2'-O-alkylribonucleotides; 2'-O-methylribonucleotides; hypoxanthine, xanthine, inosine, an abasic site; synthetic bases such as 1-(2'-deoxy-b-D-ribofuranosyl)-3-nitropyrrole; methyl phosphonate internucleotide linkage, etc. It is preferred that the presence of the modification in the template should not inhibit the DNA ligase activity more than it inhibits the DNA polymerase activity.

4) In the event that the amplification, particularly as illustrated in FIG. 1(J) is conducted so that there is no gap between polynucleotides I and IV, a non-extendible arabinosyl derivative of the nucleotide at the 3'-end of polynucleotide IV will prevent strand displacement and yet is still capable of being linked.

These findings can be used separately or in combination to arrive at conditions appropriate for each situation of polynucleotide extension and linking without encountering strand displacement.

The detectable label can be any material that is itself detectable or can be detected upon further reaction. For instance, while the detectable label can be a radioactive material, such as $^{32}P$ and $^{14}C$, it is more preferably a non-radioisotopic material. Accordingly, more preferred detectable labels are prepared from biotin or modified biotin (e.g., iminobiotin) which are incorporated into the fourth polynucleotide by well known techniques. The biotin or modified biotin can then be detected by conducting incubation with avidin or streptavidin that contains a fluorescent material or is covalently coupled with a material, such as an enzyme (e.g., alkaline phosphatase or peroxidase) that is capable of catalyzing the formation of a chromogenic product. Information describing biotin and other techniques abound in the literature and include U.S. Pat. Nos. 4,707,440 and 4,711,955, the contents of which are incorporated by reference.

Other techniques involve labeling the polynucleotide with a non-radioisotopic material that can be directly detected, such as fluorescein, tetramethyl rhodamine, Texas Red, Bodipy, Ampaca blue, or infra-red dyes. Furthermore, instead of biotin or modified biotin, digoxigenin or phenoloxazolone can be used to label the polynucleotide which is then used with an enzyme- or fluorescent-containing antibody or antibody sandwich system in order to provide a detectable signal. Although the specific labelling technique is not crucial to the understanding and use of the present invention, a labeled polynucleotide can be prepared by a transamination reaction between, for example, 2'-deoxycytidine-5'-triphosphate and 2,2'-oxybis (ethylamine) dihydrochloride according the procedure described in the art Shapiro et al, Biochem. Biophys. Res. Commun. Vol. 40, p. 839 (1970), the contents of which are incorporated by reference. Purification of the product compound by HPLC can then be followed by labeling of the derivatized nucleotide with a series of detectable moieties such as (biotin, digoxigenin, phenyloxazolone, fluorescein and tetramethylrhodamine) to give the preferred labeled nucleotide (dCTP). These derivatives can be purified by C-18 reverse-phase HPLC or ion exchange chromatography due to a large shift observed in their retention times as compared to their precursor.

Another illustrative technique which can be used to prepare a labeled nucleotide is by a similar transamination reaction between the nucleotide (e.g., 2'-deoxycytidine-5'-triphosphate) and ethylenediamine. The resulting derivatized nucleotide is then labeled with a series of detectable moieties such as fluorescein and tetramethylrhodamine to give the labeled nucleotide and the labeled nucleotide is used as is in certain aspects of the invention or is incorporated into a labeled polynucleotide in accordance with other aspects of the present invention.

To illustrate the embodiment of the invention wherein the first polynucleotide is immobilized to the solid support at its 5' end, reference is made to FIGS. 2(A)–(L) wherein common reference numbers indicate common materials. As may be seen from FIG. 2(A), the first polynucleotide indicated by I, which is at least partially complementary to the first segment, is immobilized on solid support 10 via a linker arm 11 which is selected so that the first polynucleotide is accessible for hybridization to the first segment of the target polynucleotide sequence. The linker arm can be those materials discussed with respect to the embodiment illustrated in FIGS. 1(A)–(L). However, while the linker arm can comprise nucleotides that are not complementary to the first segment of the target sequence, it cannot hybridize with the third polynucleotide due to the attachment at the 5' end.

As illustrated in FIG. 2(B), a nucleotide sequence generally indicated by 12 which includes the target nucleotide sequence is provided and the first segment generally indicated at the 13 is hybridized to the first polynucleotide. For purposes of illustration, the point mutation of the target nucleotide sequence has a first (mutant) state again indicated by T and a second (normal) state indicated by G. Once again, the nucleotide sequence can be either RNA or DNA and, if it is DNA, it is denatured so that a single strand containing the target nucleic acid sequence is provided. The target nucleotide sequence can be amplified by conventional techniques, such as PCR or LCR or Triamplification, prior to hybridization with the first polynucleotide immobilized on the solid support. However, the amount of first polynucleotide immobilized on the solid support is preferably in substantial excess of the amount of target nucleotide sequence. While the relative amounts will vary depending on the particular situation, a general molar ratio of the first polynucleotide to the first segment of the target nucleotide sequence is at least about 1:1, preferably at least about 1,000:1 and most preferably at least about 1,000,000:1.

In FIG. 2(C), the second polynucleotide indicated by II is 5' phosphorylated and is provided and hybridized to the second segment 14 of the target nucleotide sequence. The hybridization of the second polynucleotide II to the second segment 14 of the target nucleotide sequence leaves a one nucleotide gap between the 3' end of the first polynucleotide and the 5' end of the second polynucleotide. As in the previously described embodiment, the size of the gap and the relative sizes of the first and second polynucleotides are not drawn to scale.

In FIG. 2(D), free nucleotide (i.e., dATP) is provided in the presence of polymerase under conditions such that the dATP will extend the 3' end of the first polynucleotide I complementary to the T-base which forms the third segment in the mutant state of the target nucleotide sequence. Where the third segment is in the normal state indicated by G, no extension of the second polynucleotide will occur because a complementary nucleotide is not available. The polymerases described above with respect to the embodiment of FIGS. 1(A)–(L) may also be used in this embodiment.

Figure 2E:
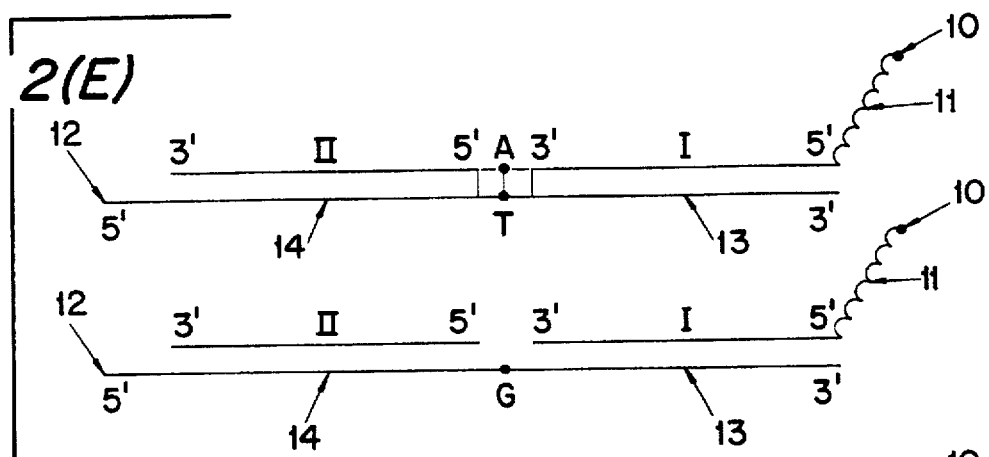

In FIG. 2(E), the extension of the first polynucleotide I is linked to the 5' end of the second polynucleotide II to form a fused product consisting of the first polynucleotide I, the second polynucleotide II and its extended portion A. Linking of the extended portion to the second polynucleotide is typically achieved using ligase. Since there is no nucleotide present to fill the gap when the third segment is in the normal state, the gap still remains where the first and second polynucleotides are bound to the target nucleotide sequence having a third segment in the normal state. Ligation may be achieved as described above with respect to the embodiment of FIGS. 1(A)–(L).

As noted above with respect to the sequence illustrated in FIGS. 1(A)–(E), if a sufficient amount of the state to be analyzed exists, the second polynucleotide II and/or the nucleotide which is complementary to the third segment of the target sequence can be labeled and the fused product detected without amplification. To the extent which they can be used in this embodiment of the invention, the other variations mentioned with respect to FIGS. 1(A)–(L) can also be used.

Figure 2F:
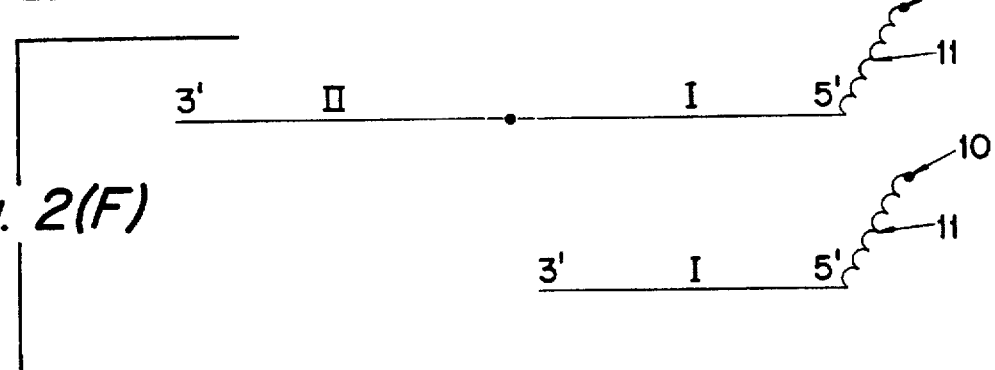

If amplification is to be conducted, at this point of the method, the fused product is separated from the target nucleotide sequence and the non-linked second polynucleotide so as to provide the structures illustrated FIG. 2(F). Separating the fused product which is immobilized on the solid support 10 can be achieved by heat denaturing and washing or by treatment with DNA helicase and then washing. The denaturing conditions are selected to separate the fused product from the target nucleic acid sequence and the non-linked first and third polynucleotides from the target nucleic acid sequence without adversely affecting the integrity of the polynucleotides or removing the fused product and the first polynucleotide from the solid support. The same techniques discussed above can be used in this embodiment of the invention as well.

Figure 2G:
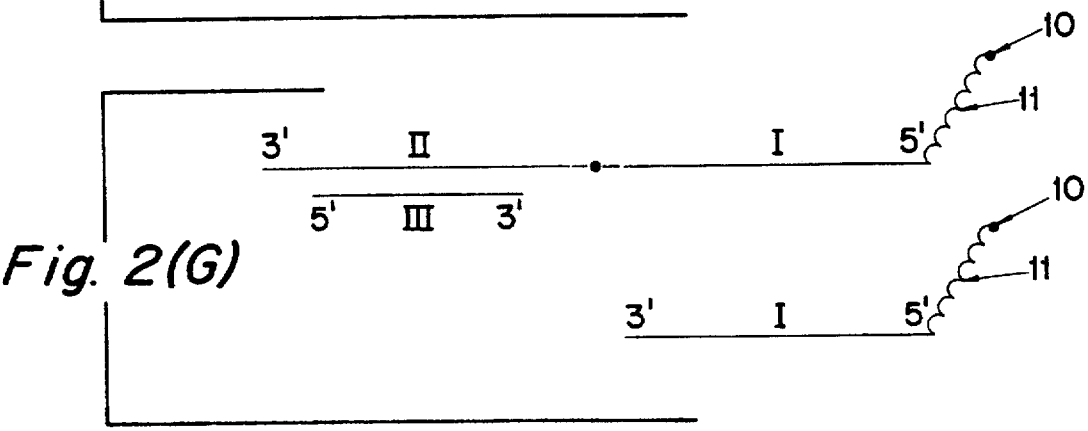

In FIG. 2(G), the third polynucleotide III is provided in an amount that is typically at least equimolar to the amount of polynucleotide I. In this illustrated embodiment, the third polynucleotide is selected such that it is complementary to a part of the portion of the fused product that is derived from the second polynucleotide II, but is not complementary to the extended portion of the first polynucleotide I. The third polynucleotide II is hybridized to the fused product immobilized on solid support 10.

Figure 2H:
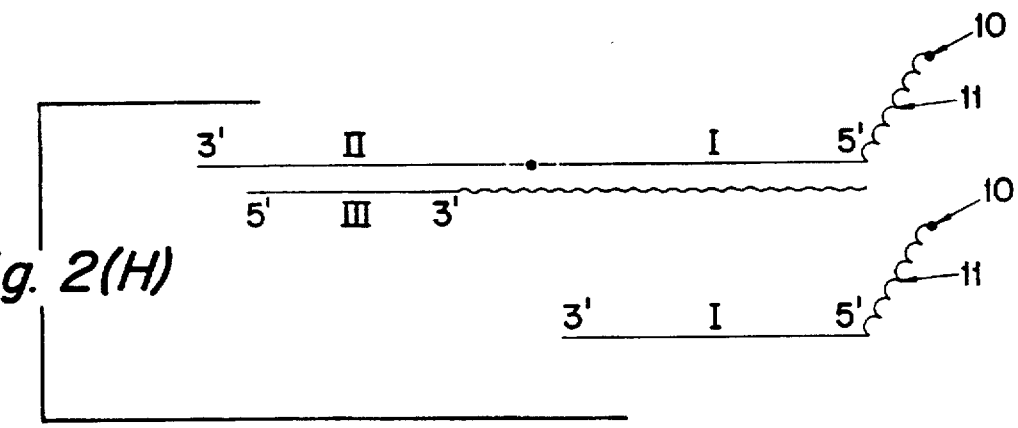

In FIG. 2(H), the third polynucleotide III is extended at its 3' end so that it is complementary to the remaining portion of the fused product immobilized on solid support 10. Extension of the third polynucleotide can again be achieved by conventional techniques such as by adding DNA polymerase and all four deoxynucleotidetriphosphates when the target nucleotide sequence is DNA.

Figure 2I:
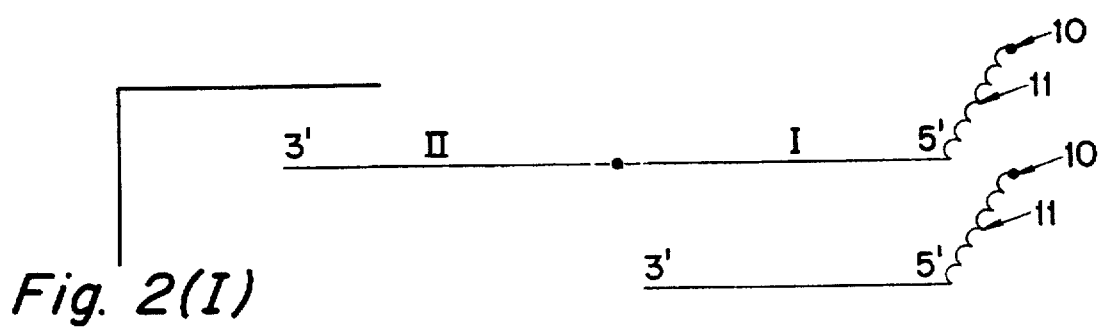

Denaturing of the third polynucleotide III in its extended form is then conducted so as to provide the structures illustrated in FIG. 2(I). Denaturing can again be conducted under conventional conditions which can be the same as those used to provide the structures illustrated in FIG. 2(F).

Figure 2J:
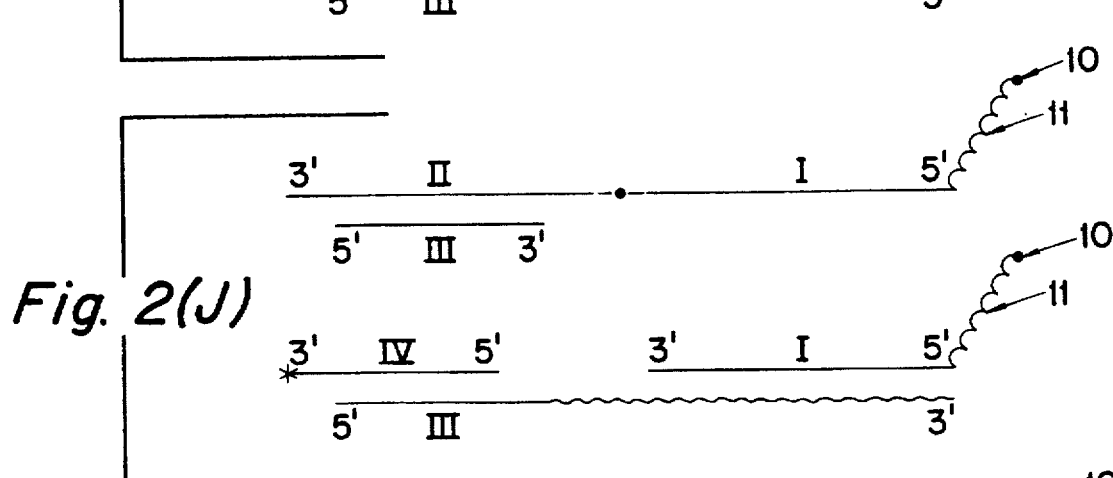
Figure 2K:
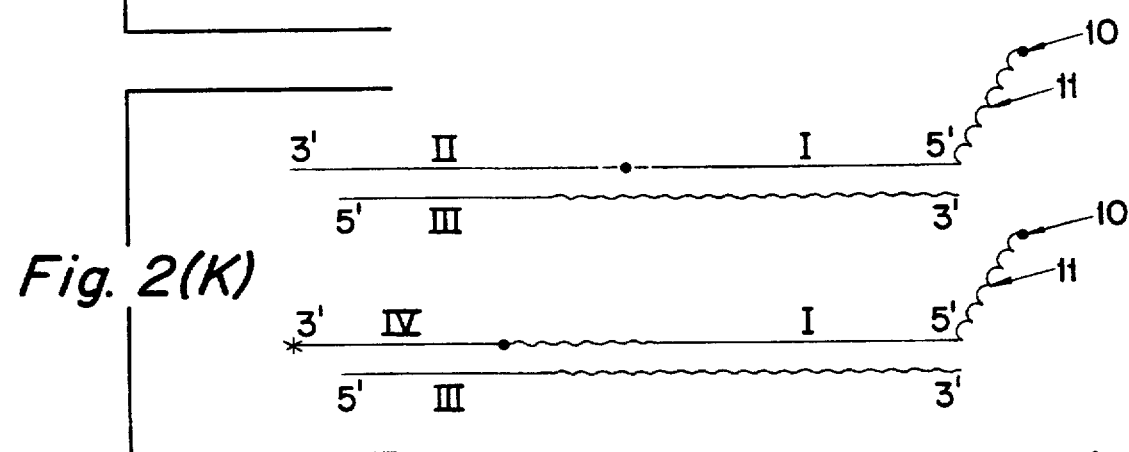

In FIG. 2(J), additional third polynucleotide III, is hybridized to the fused product mobilized on the solid support 10. In addition, the extended third polynucleotide is hybridized to the first polynucleotide I immobilized on the solid support 10 and the fourth polynucleotide IV is hybridized to the extended portion of the third polynucleotide III. The fourth polynucleotide IV contains a detectable label indicated by an asterisk. While the label is indicated at the 3' end of the fourth polynucleotide IV, it can be located at any location and can exist as a plurality of labels as long as the labels do not affect the ability of the fourth polynucleotide IV to hybridize to the extended portion of the third polynucleotide III and to be linked to the first polynucleotide. The amount of the fourth polynucleotide IV is not critical, but is generally selected such that it is at least equimolar to the amount of polynucleotide I and can be up to a ten-fold molar excess to improve hybridization kinetics.

Alternatively, the first polynucleotide I can be extended using polymerase and all four nucleotides with at least one of the nucleotides containing a detectable label so that the extended first polynucleotide I is complementary to the extended third polynucleotide III. It will be appreciated that in this embodiment of the invention, a fourth polynucleotide will not be needed.

Figure 2L:
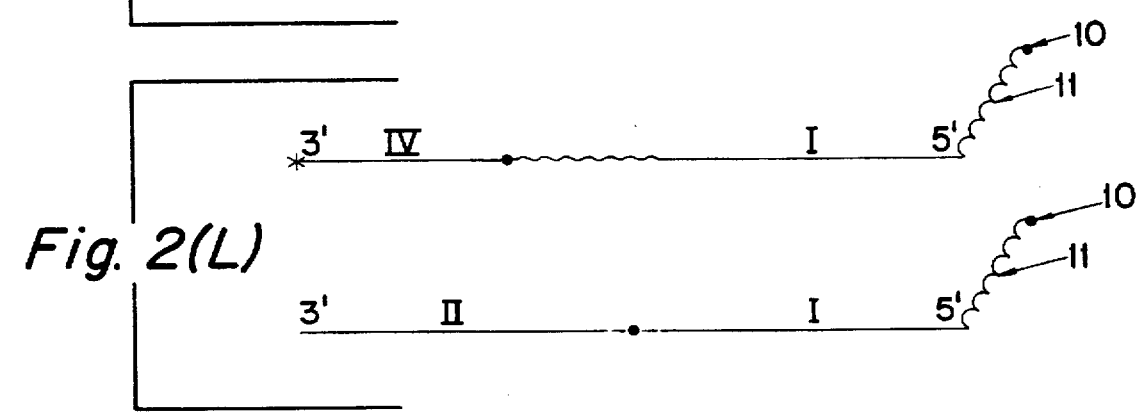

By extending the third polynucleotide III so that it is complementary to the fused product and by extending the first polynucleotide I to the fourth polynucleotide IV and linking, such as by using all four deoxynucleosidetriphosphates, DNA polymerase and DNA ligase, amplification can be achieved so as to obtain an amplified product consisting of the labeled fourth polynucleotide IV and the extended first polynucleotide I immobilized on the solid support 10 (or the labeled extended portion of polynucleotide I where a fourth polynucleotide is not used). Additionally, further amounts of extended third polynucleotide III are obtained. The steps illustrated in FIGS. 2(G)

through (K) can be repeated to obtain the desired amount of the amplified product illustrated in FIG. 2(L), as desired. The presence of the detectable label will indicate the presence of the mutant state. However, once again it should be clear that by selecting the appropriate nucleotide, the normal state can be detected instead of the mutant state.

The general materials and conditions for conducting the steps in this embodiment of the invention are the same as those described above with respect to the embodiment illustrated in FIGS. 1(A)-(L).

Figure 3A:
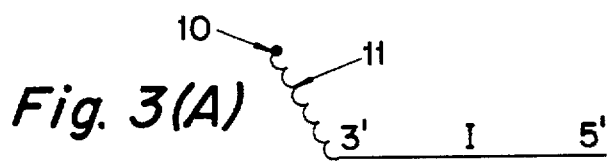
Figure 3B:
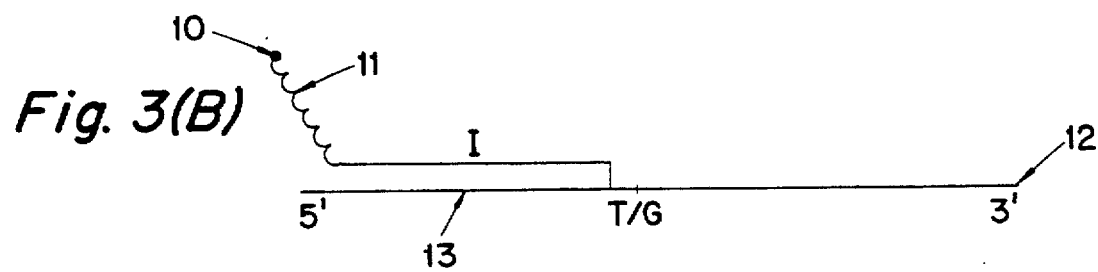
Figure 3C:
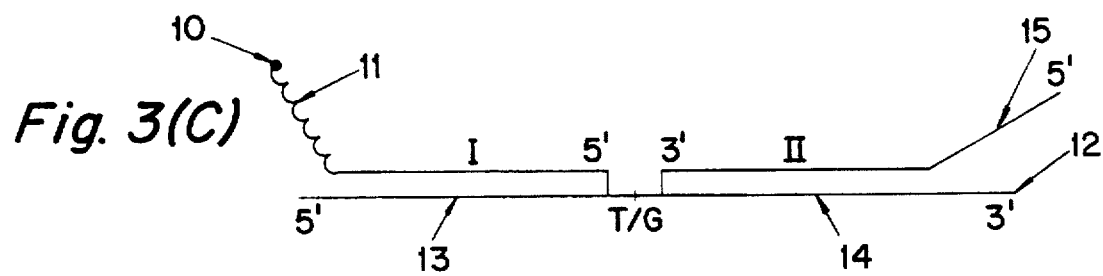
Figure 3D:
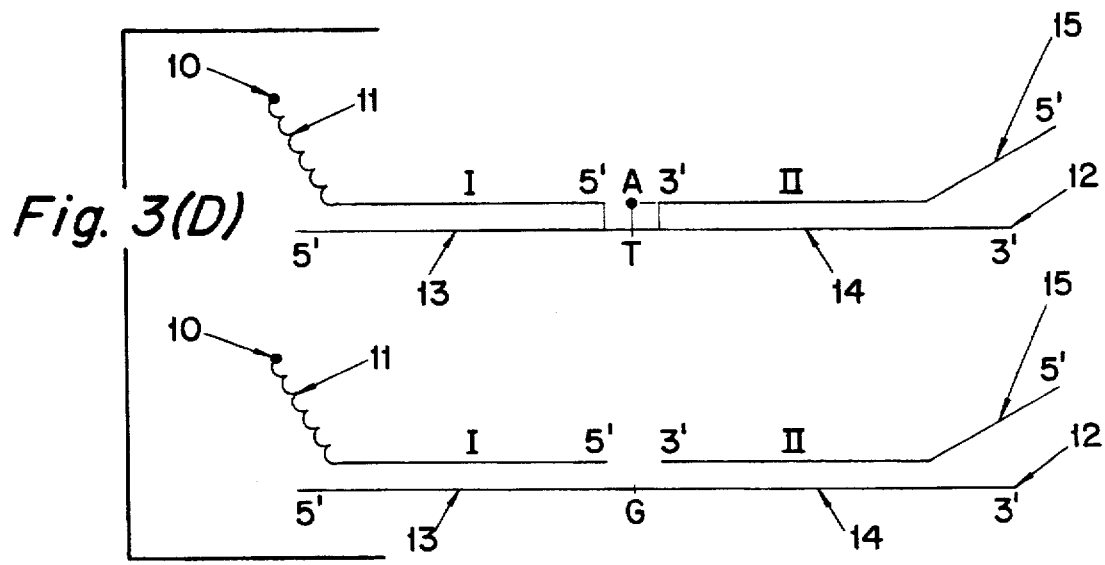

The various embodiments of the present invention can be modified to obtain yet further specificity. For instance, the embodiment illustrated in FIGS. 1(A)-(L) can be modified as illustrated in FIGS. 3(A)-(L). The steps of this modified method are similar to those for the embodiment of FIGS. 1(A)-(L) with the following exceptions. In FIG. 3(C), the second polynucleotide II includes a "tail" 15 which is selected to achieve a high level of specificity. Typically, the "tail" will be comprised of at least about 10, preferably at least about 20 bases which are not complementary to the second segment of the target sequence. The sequence of the "tail" 15 is preferably selected so that the sequence is different from sequences found in the target sequence.

The method continues similarly to the embodiment of FIGS. 1(A)-(L) until the step illustrated in FIG. 3(H) where extension of the third polynucleotide III results in the formation of the extended third polynucleotide that is complementary to at least a portion of the fused product including the extended portion and the second polynucleotide II including the "tail" 15. The portion of the extension of the third polynucleotide III that is complementary to the "tail" 15 is indicated as portion 16. As noted above, the first polynucleotide I can include a portion that is non-complementary to the first segment and the third polynucleotide III can be complementary to this portion of the first polynucleotide I. This modification can be especially used where multiple target sequences are being analyzed simultaneously.

In the step illustrated by FIG. 3(J), the fourth polynucleotide IV is provided that is complementary to at least a portion of the extended portion 16 of the third polynucleotide III. The fourth polynucleotide IV is then extended and ligated to the first polynucleotide I immobilized on the solid support. Since the fourth polynucleotide IV will only hybridize to the extended third polynucleotide III, a high level of specificity is obtained. Similar to the modification where the first polynucleotide comprises a portion that is not complementary to the first segment, where multiple target sequences are being analyzed, the "tail" of each of the second polynucleotides can be identical so that only one type of the fourth polynucleotide IV will be needed for all of the sequences being analyzed.

In order to implement the method, a kit can be provided for analyzing a target nucleotide sequence having a first segment, a second segment and a third segment therebetween which is formed of at least one nucleotide but which is formed of less than four different nucleotides wherein the third segment has a nucleotide or nucleotide sequence in a first state or a different second state. The kit comprises:

a) a first polynucleotide which is immobilized on a solid support and which is at least partially complementary to the first segment of the target nucleotide sequence;

b) a second polynucleotide which is at least partially complementary to the second segment of the target nucleotide sequence;

c) at least one nucleotide selected such that all the nucleotides which are complementary to the third segment are provided for only one of the first state or the second state and less than all the nucleotides complementary to the third segment are provided for the other state;

d) reagents suitable for forming a fused product from the first polynucleotide, second polynucleotide and the nucleotide(s);

e) a third polynucleotide complementary to at least a portion of the first polynucleotide or at least a portion of the second polynucleotide and which is capable of being extended so that it has a portion which is complementary to the other of the first or second polynucleotide;

f) material suitable for forming a product of the first polynucleotide which is complementary to at least a portion of the extended third polynucleotide, said product containing a detectable label; and g) reagents suitable for hybridizing the third polynucleotide to at least a portion of the first polynucleotide or second polynucleotide, for extending the third polynucleotide, and for forming the labeled product of the first polynucleotide.

The product referred in part f) includes those instances where a fourth polynucleotide is used which can be extended and ligated to the first polynucleotide as illustrated in FIGS. 1(A)-(L) or 3(A)-(L), those instance where a fourth polynucleotide is hybridized and the first polynucleotide is extended and ligated to the fourth polynucleotide as illustrated in FIGS. 2(A)-(L) and those instances where a fourth polynucleotide is not used and the first polynucleotide is extended as described above.

The reagents can be selected from those disclosed above or other reagents known to those skilled in the art which can be selected to conduct the method of the present invention. In addition, the kit may contain other materials commonly used in the process, such as deionized water, to further ensure the accuracy of the results.

From the foregoing discussion, those skilled in the art will recognize that the present invention is a significant advance in the art, particularly over techniques where the nucleic acid sequence being analyzed is immobilized on a solid support. Since any target nucleic acid sequence which does not result in the "filling in" of the gap complementary to the third segment will be separated from the fused product that is immobilized on the solid support prior to amplification, the present invention can provide a true screening test for mutations that are essentially limited only by primarily the fidelity of the polymerase and secondarily the fidelity of the joining reagent used. Thus, one can use the present invention to detect mutations that can be present in only one of every $10^5$ occurrences or even in one of every $10^6$ or $10^7$ occurrences.

The following theoretical example is presented in order to more fully illustrate one embodiment of the invention analyzing multiple possible point mutations in the p53 gene in a DNA sample from a patient using a biochip with four polynucleotides immobilized on a polypropylene support. It should in no way be construed, however, as limiting the broad scope of the invention.

With reference to the portions of the genomic DNA sequence of the human p53 gene illustrated in FIG. 4, the sequence is a portion of the sequence obtained from GenBank (ID: HSP53G standard; DNA; PRI; 20303 BP. AC X54156) wherein base 1 of FIG. 4A corresponds to base 11601 of the Genbank sequence and base 1 of FIG. 4B corresponds to base 12951 of the Genbank sequence. Information relating to p53 (also called transformation-associated protein 53, cellular tumor antigen p53, and non-viral tumor antigen p53) can be found in Mol. Cell. Biol. 6:1379–1385 (1986) and Mol. Cell. Biol. 7:961–963 (1987), the contents of which are incorporated by reference. For the illustrated portions of the genomic p53 gene, assume that the following mutations in a DNA sample from a patient are to be analyzed:

| Base Position | Wild Type Sequence | Mutation |
|---|---|---|
| 467 (Seq. ID No. 1) | A | T |
| 605 (Seq. ID No. 1) | C | A |
| 163 (Seq. ID No. 2) | T | G |
| 267 (Seq. ID No. 2) | G | C |

If FIGS. 4A and 4B, the exons in which these possible mutation sites occur are indicated by underlining.

Figure 5A:
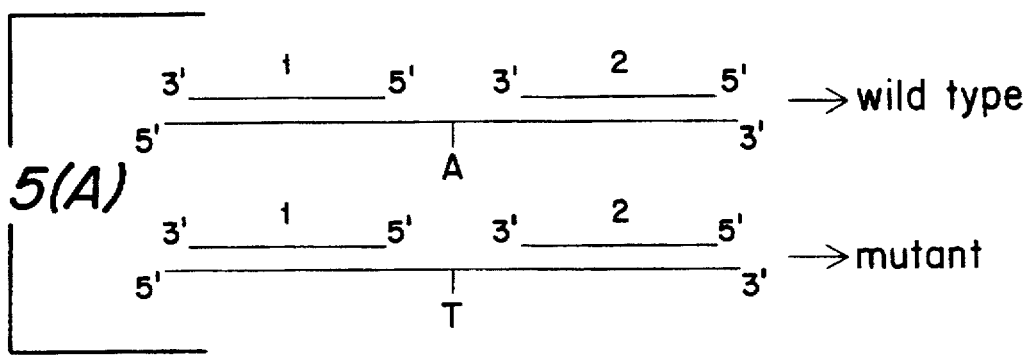
FIGS. 5(A)-(D) illustrate an embodiment wherein multiple target sequences are analyzed.

Referring to FIG. 5(A), polynucleotides 1 and 2 are designed so as to hybridize to the p53 gene in such a way that there is a one nucleotide gap between polynucleotide 1 and polynucleotide 2. The gap refers to the position 467 on the portion of the p53 gene illustrated in FIG. 4A and Seq. ID No. 1.

Figure 5B:
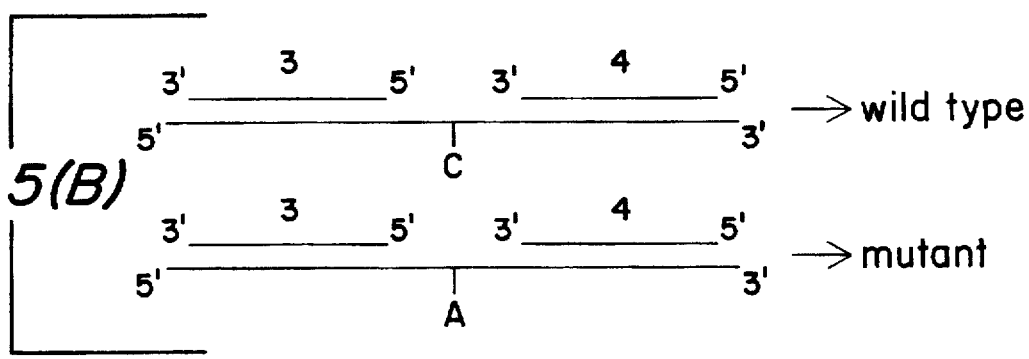
Figure 5C:
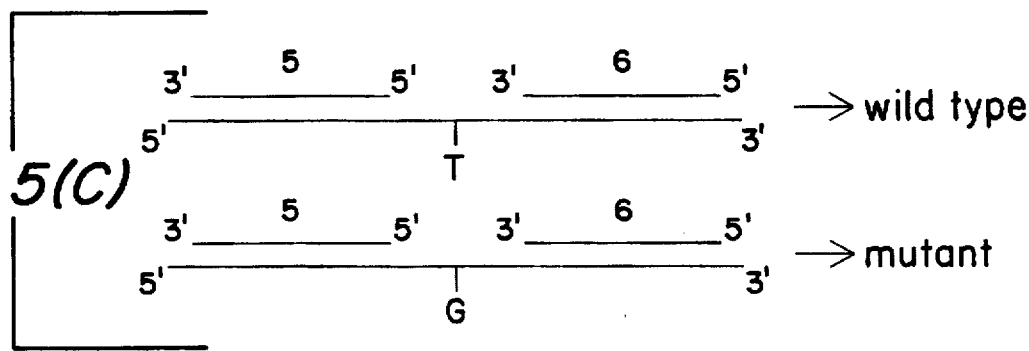
Figure 5D:
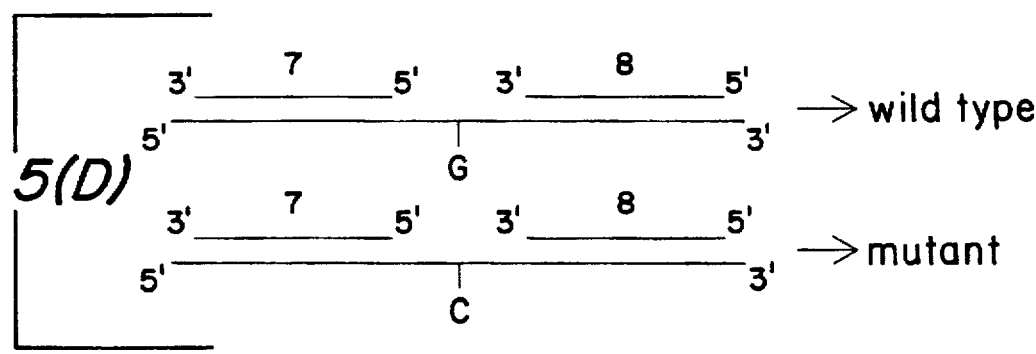

Similarly, in FIG. 5(B), polynucleotides 3 and 4 hybridize to the p53 gene and so that there is a one nucleotide gap. The gap corresponds to the position 605 on the portion of the p53 gene illustrated in FIG. 4A and Seq. ID No. 1.

Likewise, polynucleotides 5 and 6 will be used for analyzing the sequence at position 163 and polynucleotides 7, 8 for position 267 on the portion of the p53 gene illustrated in FIG. 4B and Seq. ID No. 2.

Figure 6:
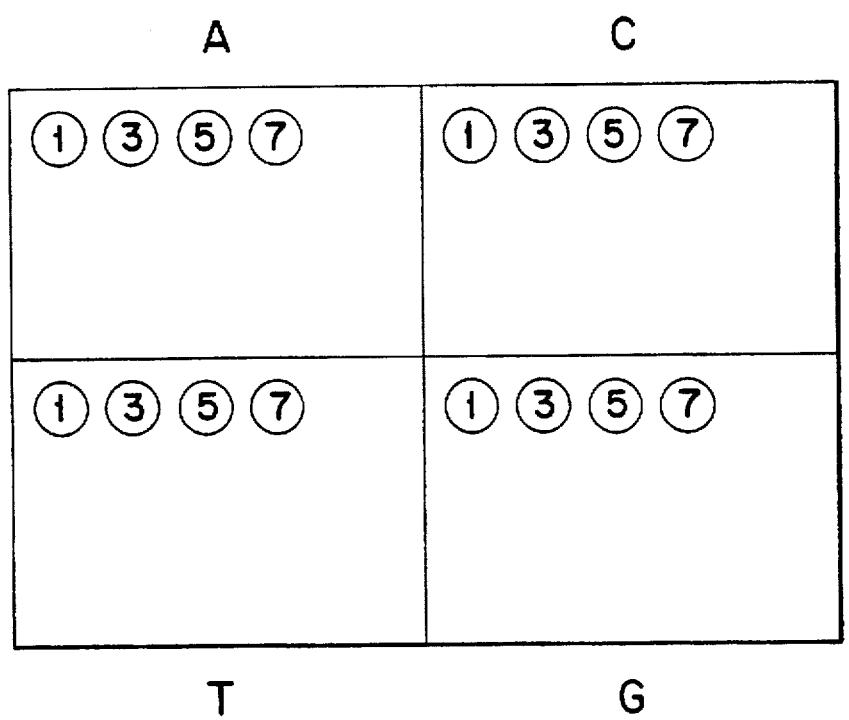
FIG. 6 illustrates a solid support with multiple first polynucleotides immobilized thereon and divided into different sections.

A chip will be designed which has four identical grids of mobilized polynucleotides (FIG. 6). Positions 1, 3, 5 and 7 on each section of the chip corresponds to polynucleotides 1, 3, 5, and 7 immobilized from their 5'-end. The method involves the following steps:

Step 1: Add polynucleotides 2, 4, 6 and 8 along with the DNA sample, to all four sections of the chip.

Step 2: Denature (by heating) and then reduce the temperature and allow the polynucleotides to hybridize to their respective targets on the DNA. Polynucleotides 2, 4, 6 and 8 may hybridize to all the target molecules on the chip. However, one nucleotide gap structures of paired polynucleotides [1:2, 3:4, 5:6, 7:8] will form only at positions 1, 3, 5 and 7.

Step 3: Add DNA polymerase and DNA ligase to all four sections. Add only dATP to section A, dCTP to section C, dTTP to section T, and dGTP to section G. Any DNA polymerase can be used, such as T4, T7, E. coli Pol I Pol I Klenow, Taq, Pfu, etc. A DNA polymerase having 3'–5' exonuclease activity and devoid of 5'–3' exonuclease activity is preferably used. With respect to the ligase, T-4 ligase, E. coli ligase, Taq ligase, Pfu ligase can be used. The preferred ligase would be the one which has the least mismatch ligation and ligation across the gap activity.

The deoxynucleoside triphosphate concentration will be determined by the Km and fidelity of the particular DNA polymerase used.

In section A, at grid position 1, when there is a mutation in the p53 gene at position 467, then DNA polymerase will incorporate dAMP at the 3' end of the polynucleotide 2 and then DNA ligase will ligate the 5' end of polynucleotide 1 to extended polynucleotide 2. Also at position 5, dAMP will be added to the 3' end of the polynucleotide 6 (hybridized to the wild type sequence) and will be ligated to the 5' end of polynucleotide 5. No incorporation of dAMP and ligation will occur at position 3 and position 7.

In section C, at grid position 3, if there is a mutation in the p53 gene at position 163, the dCMP will be incorporated into polynucleotide 6 and extended polynucleotide 6 will ligate to the 5' end of polynucleotide 5. At grid position 7, polynucleotide 8 hybridized to wild type p53 will be extended by adding dCMP and then ligated to polynucleotide 7. No dCMP incorporation will occur at any other position.

In section G, at grid position 7, if the p53 gene has a mutation at nucleotide 267, then DNA polymerase will incorporated dGMP at the 3' end of polynucleotide 8 and extended polynucleotide 8 will be ligated to the 5' end of polynucleotide 7. Also at grid position 3, DNA polymerase will add dGMP to the 3' end of polynucleotide 4 and DNA ligase will seal the nick between polynucleotides 3 and 4.

Section T, at grid position 3, if the p53 mutant sequence at position 605 is present in the sample, the a dTMP will be added to the 3' end of polynucleotide 4. DNA ligase will close the nick between the extended polynucleotides 4 and 3. At grid position 1, a dTMP will be incorporated into the 3' end polynucleotide 2 hybridized to p53 having wild type sequence at position 467. The extended polynucleotide 2 will be ligated to the 5' end of polynucleotide 1.

Only positions where an immobilized polynucleotide is ligated to the adjacent extended polynucleotide are the sections where a dNTP complementary either to the wild type or mutant sequence is present.

Step 4: Remove the free polynucleotides and the target DNA by either denaturing and washing or by treating with 3'–5' exonuclease and washing or by washing in the presence of an electric field or a combinations thereof. This step should leave only extended polynucleotide ligated to the immobilized polynucleotide on the chip.

Step 5: The extended and ligated product from the previous step can be amplified as explained in the FIGS. 1(G)–(L).

Step 6: The presence of amplified product at specific position on grid will indicate the presence of a particular sequence.

The presence of amplified product at Section A, grid position 1, indicates the presence of a T at position 467 of the p53 gene. Similarly, presence of amplified product at Section A, grid position 5, indicates that there is a T at position 163 of the p53 gene. Thus, the detection of amplified product will indicate the presence of a sequence and in the absence of a particular sequence, no amplification will take place. The whole process can be automated by using robotic arms and a computerized detection system.

Although preferred embodiments of the invention have been described above, it will be appreciated that many modifications and variations of the present invention are possible in light of the above teachings and within the purview of the appended claims without departing from the spirit and intended scope of the invention.

We claim:

1. A method for analyzing a target nucleotide sequence having a first segment, a second segment and a third segment therebetween which third segment is formed of at least one nucleotide but which is formed of less than four different nucleotides wherein the third segment has a nucleotide or nucleotide sequence in a first state or a different second state, said method comprising:
   a) providing a first polynucleotide which is immobilized on a solid support and which is at least partially complementary to the first segment of the target nucleotide sequence;
   b) hybridizing the first polynucleotide to the first segment of the target nucleotide sequence under conditions suitable for hybridization;
   c) providing a second polynucleotide which is at least partially complementary to the second segment of the target nucleotide sequence;
   d) hybridizing the second polynucleotide to the second segment of the target nucleotide sequence under conditions suitable for hybridization wherein a gap of at least one nucleotide is present between one end of the first polynucleotide and one end of the second polynucleotide;
   e) providing at least one nucleotide selected such that all the nucleotides which are complementary to the third segment are provided for only one of the first state or the second state and less than all the nucleotides complementary to the third segment are provided for the other state, the nucleotide or nucleotides being provided under conditions whereby the nucleotide or nucleotides form an extended portion of one of the first or second polynucleotide that is complementary to the nucleotides(s) of the third segment of the target nucleic acid sequence in one of the states;
   f) linking the polynucleotide with the extended portion to the other polynucleotide under conditions whereby a fused product is formed comprised of the first polynucleotide, the second polynucleotide and the extended portion therebetween;
   g) separating the fused product from the target nucleotide sequence and any non-linked second polynucleotide by treatment with exonuclease to digest target nucleotide sequence and non-linked second polynucleotide, and washing;
   h) amplifying at least a portion of the fused product wherein the portion contains the extended portion under conditions suitable to form an amplified product containing the first polynucleotide and a detectable label, the amplifying being conducted to obtain a sufficient quantity of amplified product to detect the detectable label; and
   i) detecting the presence of the label of the amplified product.

2. The method of claim 1 wherein the support is selected from the group consisting of glass, cellulosic material and polymeric material.

3. The method of claim 2 wherein the cellulosic material is nitrocellulose.

4. The method of claim 2 wherein the polymeric material is selected from the group consisting of polystyrene, polypropylene, polyethylene, dextran, polyamide, polyacrylamide, and agarose.

5. The method of claim 1 wherein the target nucleotide sequence is present in a DNA strand which has been denatured before being hybridized to the first polynucleotide.

6. The method of claim 1 wherein the first and second polynucleotides are provided simultaneously.

7. The method of claim 1 wherein the third segment consists of a single nucleotide.

8. The method of claim 1 wherein steps e) and f) are conducted simultaneously in the presence of polymerase and ligase.

9. The method of claim 1 wherein step g) is conducted by denaturing the fused product from the target nucleotide sequence and washing.

10. The method of claim 1 wherein the amplification of step h) is conducted by:
    i) hybridizing a third polynucleotide to the fused product;
    ii) extending the third polynucleotide so that the extended third polynucleotide is complementary to the extended portion of the fused product and at least a portion of the first polynucleotide and the second polynucleotide of the fused product;
    iii) separating the extended third polynucleotide from the fused product;
    iv) providing a fourth polynucleotide which contains a detectable label and is at least partially complementary to the extended portion of the third polynucleotide;
    v) linking the fourth polynucleotide with the first polynucleotide to form the amplified product; and
    vi) repeating steps i) through v) to obtain a sufficient quantity of the amplified product to detect the detectable label.

11. The method of claim 10 wherein the third poly nucleotide is complementary to at least the extended portion of the fused product.

12. The method of claim 10 wherein the fourth polynucleotide is linked with the first polynucleotide in the presence of polymerase, ligase and four different nucleotides.

13. The method of claim 1 wherein the detectable label is selected from the group consisting of biotin, digoxigenin, phenyloxazolone, and fluorescing material.

14. The method of claim 1 wherein the first polynucleotide is immobilized on the solid support so that the 5' end is adjacent the gap.

15. The method of claim 1 wherein the first polynucleotide is immobilized on the solid support so that the 3' end is adjacent the gap.

16. The method of claim 1 wherein the target nucleotide sequence is DNA.

17. The method of claim 1 wherein the first polynucleotide is immobilized on the solid support so that the 3' end is adjacent the gap and amplification of step h) is conducted by:
    i) hybridizing a third polynucleotide to the fused product;
    ii) extending the third polynucleotide so that the extended third polynucleotide is complementary to the extended portion of the fused product and at least a portion of the first polynucleotide and the second polynucleotide of the fused product;

iii) separating the extended third polynucleotide from the fused product;

iv) providing polymerase and nucleotides, at least one of the nucleotides containing a detectable label, and extending the first polynucleotide to be complementary to the extended third polynucleotide so as to form the amplified product;

v) repeating steps i) through iv) to obtain a sufficient quantity of the amplified product to detect the detectable label.

18. The method of claim 1 wherein subsequent to the amplification step h), the solid support is treated to remove materials not immobilized thereon.

19. The method of claim 1 wherein the solid support is comprised of polypropylene.

20. The method of claim 1 wherein the first and second polynucleotides are hybridized to the first and second segments simultaneously.

21. The method of claim 1 wherein the second polynucleotide has a 3' end adjacent the gap and has a portion at the 5' end which is not complementary to any portion of the target nucleotide sequence and wherein the amplification also amplifies the non-complementary portion of the second polynucleotide.

22. The method of claim 21 wherein the amplification of step h) is conducted by:

i) hybridizing a third polynucleotide to the fused product;

ii) extending the third polynucleotide so that the extended third polynucleotide is complementary to the extended portion of the fused product and at least a portion of the first polynucleotide and the second polynucleotide of the fused product including the non-complementary portion of the second polynucleotide;

iii) separating the extended third polynucleotide from the fused product;

iv) providing a fourth polynucleotide which is at least partially complementary to the extended portion of the third polynucleotide which is complementary to the non-complementary portion of the second polynucleotide;

v) extending the fourth polynucleotide to the first polynucleotide;

vi) linking the fourth polynucleotide with the first polynucleotide to form the amplified product containing the detectable label; and vii) repeating steps i) through vi) to obtain a sufficient quantity of the amplified product to detect the detectable label.

23. The method of claim 22 wherein the fourth polynucleotide contains the detectable label.

24. The method of claim 23 wherein the polynucleotide having a 3' end adjacent the gap is modified so that the 3' terminal nucleotide is a dideoxynucleotide.

25. The method of claim 1 wherein multiple target nucleotide sequences are analyzed simultaneously.

26. The method of claim 25 wherein a first polynucleotide immobilized on a solid support is provided for each target sequence analyzed and the solid support is divided into a grid and wherein step (e) is conducted by providing a different single nucleotide in each section of the grid.

27. A method for analyzing a target nucleotide sequence having a first segment, a second segment and a third segment therebetween which third segment is formed of at least one nucleotide but which is formed of less than four different nucleotides wherein the third segment has a nucleotide or nucleotide sequence in a first state or a different second state, said method comprising:

a) providing a first polynucleotide which is immobilized on a solid support and which is at least partially complementary to the first segment of the target nucleotide sequence;

b) providing a second polynucleotide which is at least partially complementary to the second segment of the target nucleotide sequence;

c) hybridizing the second polynucleotide to the second segment of the target nucleotide sequence under conditions suitable for hybridization;

d) providing at least one nucleotide selected such that all the nucleotides which are complementary to the third segment are provided for only one of the first state or the second state and less than all the nucleotides complementary to the third segment are provided for the other state, the nucleotide or nucleotides being provided under conditions whereby the nucleotide or nucleotides form an extended portion of the second polynucleotide that is complementary to the nucleotides(s) of the third segment of the target nucleic acid sequence in one of the states;

e) hybridizing the first polynucleotide to the first segment of the target nucleotide sequence under conditions suitable for hybridization;

f) linking the polynucleotide with the extended portion to the other polynucleotide under conditions whereby a fused product is formed comprised of the first polynucleotide, the second polynucleotide and the extended portion therebetween;

g) separating the fused product from the target nucleotide sequence and any non-linked second polynucleotide by treatment with exonuclease to digest target nucleotide sequence and non-linked second polynucleotide, and washing;

h) amplifying at least a portion of the fused product wherein the portion contains the extended portion under conditions suitable to form an amplified product containing the first polynucleotide and a detectable label, the amplifying being conducted to obtain a sufficient quantity of amplified product to detect the detectable label; and i) detecting the presence of the label of the amplified product.

28. The method of claim 27 wherein subsequent to the amplification step h), the solid support is treated to remove materials not immobilized thereon.

29. The method of claim 27 wherein the solid support is comprised of polypropylene.

30. The method of claim 27 wherein the amplified product comprises the first polynucleotide and a labeled polynucleotide.

31. The method of claim 27 wherein the second polynucleotide has a 3' end adjacent the gap and has a portion at the 5' end which is not complementary to any portion of the target nucleotide sequence and wherein the amplification also amplifies the non-complementary portion of the second polynucleotide.

32. The method of claim 31 wherein the amplification of step h) is conducted by:

i) hybridizing a third polynucleotide to the fused product;

ii) extending the third polynucleotide so that the extended third polynucleotide is complementary to the extended portion of the fused product and at least a portion of the first polynucleotide and the second polynucleotide of the fused product including the non-complementary portion of the second polynucleotide;

iii) separating the extended third polynucleotide from the fused product;

iv) providing a fourth polynucleotide which is at least partially complementary to the extended portion of the third polynucleotide which is complementary to the non-complementary portion of the second polynucleotide;

v) extending the fourth polynucleotide to the first polynucleotide;

vi) linking the fourth polynucleotide with the first polynucleotide to form the amplified product containing the detectable label; and vii) repeating steps i) through vi) to obtain a sufficient quantity of the amplified product to detect the detectable label.

33. The method of claim 32 wherein the fourth polynucleotide contains the detectable label.

34. The method of claim 27 wherein multiple target nucleotide sequences are analyzed simultaneously.

35. The method of claim 34 wherein a first polynucleotide immobilized on a solid support is provided for each target sequence analyzed and the solid support is divided into a grid and wherein step (d) is conducted by providing a different single nucleotide in each section of the grid.

36. The method of claim 27 wherein the third segment consists of a single nucleotide.

37. The method of claim 27 wherein the target nucleotide sequence is DNA.

38. A method for analyzing a target nucleotide sequence having a first segment, a second segment and a third segment therebetween which third segment is formed of at least one nucleotide but which is formed of less than four different nucleotides wherein the third segment has a nucleotide or nucleotide sequence in a first state or a different second state, said method comprising:

a) providing a first polynucleotide which is immobilized on a solid support and which is at least partially complementary to the first segment of the target nucleotide sequence;

b) hybridizing the first polynucleotide to the first segment of the target nucleotide sequence under conditions suitable for hybridization;

c) providing a second polynucleotide which is at least partially complementary to the second segment of the target nucleotide sequence;

d) hybridizing the second polynucleotide to the second segment of the target nucleotide sequence under conditions suitable for hybridization wherein a gap of at least one nucleotide is present between one end of the first polynucleotide and one end of the second polynucleotide, and wherein the polynucleotide having a 3' end adjacent the gap is modified so that ligation across the gap is inhibited;

e) providing at least one nucleotide selected such that all the nucleotides which are complementary to the third segment are provided for only one of the first state or the second state and less than all the nucleotides complementary to the third segment are provided for the other state, the nucleotide or nucleotides being provided under conditions whereby the nucleotide or nucleotides form an extended portion of one of the first or second polynucleotide that is complementary to the nucleotides(s) of the third segment of the target nucleic acid sequence in one of the states;

f) linking the polynucleotide with the extended portion to the other polynucleotide under conditions whereby a fused product is formed comprised of the first polynucleotide, the second polynucleotide and the extended portion therebetween;

g) separating the fused product from the target nucleotide sequence and any non-linked second polynucleotide;

h) amplifying at least a portion of the fused product wherein the portion contains the extended portion under conditions suitable to form an amplified product containing the first polynucleotide and a detectable label, the amplifying being conducted to obtain a sufficient quantity of amplified product to detect the detectable label; and i) detecting the presence of the label of the amplified product.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 800 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
TGTTGGGGGA GGGGCCTCCT CCTCTGCAGG CCCAGGTGAC CCAGGGTTGG AAGCGTCTCA     60
TGCTGGATCC CCACTTTTCC TCTTGCAGCA GCCAGACTGC CTTCCGGGTC ACTGCCATGG    120
AGGAGCCGCA GTCAGATCCT AGCGTCGAGC CCCCTCTGAG TCAGGAAACA TTTTCAGACC    180
TATGGAAACT GTGAGTGGAT CCATTGGAAG GGCAGGCCAC CACCCCGACC CCAACCCCAG    240
CCCCCTAGCA GAGACCTGTG GGAAGCGAAA ATTCATGGGA CTGACTTTCT GCTCTTGTCT    300
TTCAGACTTC CTGAAAACAA CGTTCTGGTA AGGACAAGGG TTGGGCTGGG ACCTGGAGGG    360
CTGGGGGGC TGGGGGGCTG AGGACCTGGT CCTCTGACTG CTCTTTTCAC CCATCTACAG    420
TCCCCCTTGC CGTCCCAAGC AATGGATGAT TTGATGCTGT CCCCGGACGA TATTGAACAA    480
TGGTTCACTG AAGACCCAGG TCCAGATGAA GCTCCCAGAA TGCCAGAGGC TGCTCCCCGC    540
GTGGCCCCTG CACCAGCAGC TCCTACACCG GCGGCCCTG CACCAGCCCC CTCCTGGCCC    600
CTGTCATCTT CTGTCCCTTC CCAGAAAACC TACCAGGGCA GCTACGGTTT CCGTCTGGGC    660
TTCTTGCATT CTGGGACAGC CAAGTCTGTG ACTTGCACGG TCAGTTGCCC TGAGGGGCTG    720
GCTTCCATGA GACTTCAATG CCTGGCCGTA TCCCCCTGCA TTTCTTTTGT TTGGAACTTT    780
GGGATTCCTC TTCACCCTTA                                                800
```

( 2 ) INFORMATION FOR SEQ ID NO:2:

( i ) SEQUENCE CHARACTERISTICS:
        ( A ) LENGTH: 600 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
AGGAGGTGCT TACACATGTT TGTTTCTTTG CTGCCGTGTT CCAGTTGCTT TATCTGTTCA     60
CTTGTGCCCT GACTTTCAAC TCTGTCTCCT TCCTCTTCCT ACAGTACTCC CCTGCCCTCA    120
ACAAGATGTT TTGCCAACTG GCCAAGACCT GCCCTGTGCA GCTGTGGGTT GATTCCACAC    180
CCCCGCCCGG CACCCGCGTC CGCGCCATGG CCATCTACAA GCAGTCACAG CACATGACGG    240
AGGTTGTGAG GCGCTGCCCC CACCATGAGC GCTGCTCAGA TAGCGATGGT GAGCAGCTGG    300
GGCTGGAGAG ACGACAGGGC TGGTTGCCCA GGGTCCCAG GCCTCTGATT CCTCACTGAT    360
TGCTCTTAGG TCTGGCCCCT CCTCAGCATC TTATCCGAGT GGAAGGAAAT TTGCGTGTGG    420
AGTATTTGGA TGACAGAAAC ACTTTTCGAC ATAGTGTGGT GGTGCCCTAT GAGCCGCCTG    480
```

```
AGGTCTGGTT  TGCAACTGGG  GTCTCTGGGA  GGAGGGGTTA  AGGGTGGTTG  TCAGTGGCCC     540

TCCGGGTGAG  CAGTAGGGGG  GCTTTCTCCT  GCTGCTTATT  TGACCTCCCT  ATAACCCAT      600
```